US010052404B2

(12) United States Patent
Ahlberg et al.

(10) Patent No.: US 10,052,404 B2
(45) Date of Patent: Aug. 21, 2018

(54) BIOCOMPATIBLE COMPONENT

(75) Inventors: Elisabet Ahlberg, Västra Frölunda (SE); Ingela Mattisson, Torslanda (SE); Johanna Löberg, Göteborg (SE)

(73) Assignee: Dentsply Sirona Inc., York, PA (US)

( * ) Notice: Subject to any disclaimer, the term of this patent is extended or adjusted under 35 U.S.C. 154(b) by 139 days.

(21) Appl. No.: 13/468,243

(22) Filed: May 10, 2012

(65) Prior Publication Data

US 2012/0288699 A1 Nov. 15, 2012

Related U.S. Application Data

(60) Provisional application No. 61/484,951, filed on May 11, 2011.

(30) Foreign Application Priority Data

May 11, 2011 (EP) .................................... 11165686

(51) Int. Cl.
*A61L 27/04* (2006.01)
*A61L 27/06* (2006.01)
*A61L 27/30* (2006.01)
*A61L 24/00* (2006.01)

(52) U.S. Cl.
CPC .............. *A61L 27/04* (2013.01); *A61L 24/00* (2013.01); *A61L 27/06* (2013.01); *A61L 27/30* (2013.01); *A61L 27/306* (2013.01); *A61L 2400/18* (2013.01); *A61L 2430/02* (2013.01); *Y10T 428/25* (2015.01); *Y10T 428/2982* (2015.01)

(58) Field of Classification Search
CPC .............. B32B 5/16; B32B 7/02; A61L 27/04
USPC ......................................... 428/220, 402, 323
See application file for complete search history.

(56) References Cited

U.S. PATENT DOCUMENTS

| 5,460,701 A * | 10/1995 | Parker et al. ................. 204/164 |
| 6,440,383 B1 | 8/2002 | Duyvesteyn et al. |
| 2003/0059742 A1 | 3/2003 | Webster et al. |
| 2006/0161256 A1 | 7/2006 | Ziegler et al. |
| 2007/0259427 A1 | 11/2007 | Storey |
| 2009/0270997 A1 * | 10/2009 | Bignozzi et al. ............. 623/23.6 |
| 2010/0174382 A1 * | 7/2010 | Gretzer ................. A61L 27/306 623/23.53 |

FOREIGN PATENT DOCUMENTS

| CN | 101604870 A | 12/2009 |
| DE | 2009016554 A1 | 9/2010 |
| WO | 2008054408 A2 | 5/2008 |
| WO | 20080078164 A2 | 7/2008 |
| WO | 2009040124 A1 | 4/2009 |

OTHER PUBLICATIONS

Osteoblast, Anselme K; adhesion on biomaterials, Biomaterials 21, 667-681 (2000).
Zareen Abbas, Christophe Labbez, Sture Nordholm, & Elisabet Ahlberg;J. Phys. Chem. C 2008, 112, 5715-5723.
Zareen Abbas, J. Perez Holmberg, A,-K. Physiochem. Eng. Aspects, 2011, doi: 10.1016/j.colsurfa.2011.03.064.
Perez Holmberg, Z. Abbas, E. Ahlberg, M. Hassellov & J. Bergenholtz, J. Phys. Chem. C, 2011.
I. Matisson & E. Ahlberg, Appl. Surf. Sci., 2011, Accepted for publication.
A.P. Do Serro, A.C. Fernandes & V.S.B. de Jesus, J. Biomed. Mater. Res., 2000,49, 345-352.
Z.Z. Zyman, D.V. Rokhmistrov & V.I. Glushko, J. Mater. Med., 2010, 21, 123-130.
T.Kokubo & H. Takadama, Biomaterials, 2006, 27, 2907-2915.
Abbas et al, Nanoparticles Colloids & Surfaces A: Physiochem. Eng. Aspects 384 (2011) 254-261.
Stanford, Jacobson et al, 1995, Journal of Biological Chenistry 270 (16): 9420-9428.
Schneider, Zaharias et al., 2004. Journal of Biomedical Materials research. 69A 3:462-468.
Journal of Inorganic materials vol. 15, No. 1; Feb. 2000 Preparation of Nanosized Tio2 Powders from Hydrolysis of TiC14 (with English Abstract) Zhang.
Y. Yang, Jul. 2006 JOM, Enhancing Osseointegration . . . .
International Search Report.
PCT Written Opinion.
European Search Report dated Oct. 27, 2011.

* cited by examiner

*Primary Examiner* — Lawrence Ferguson
(74) *Attorney, Agent, or Firm* — Douglas J. Hura; Leana Levin; David A. Zdurne

(57) ABSTRACT

The invention provides a biocompatible component having a surface intended for contact with living tissue, wherein the surface comprises particles of metal oxide, said particles having an average particle size of less than 100 nm.

33 Claims, 17 Drawing Sheets

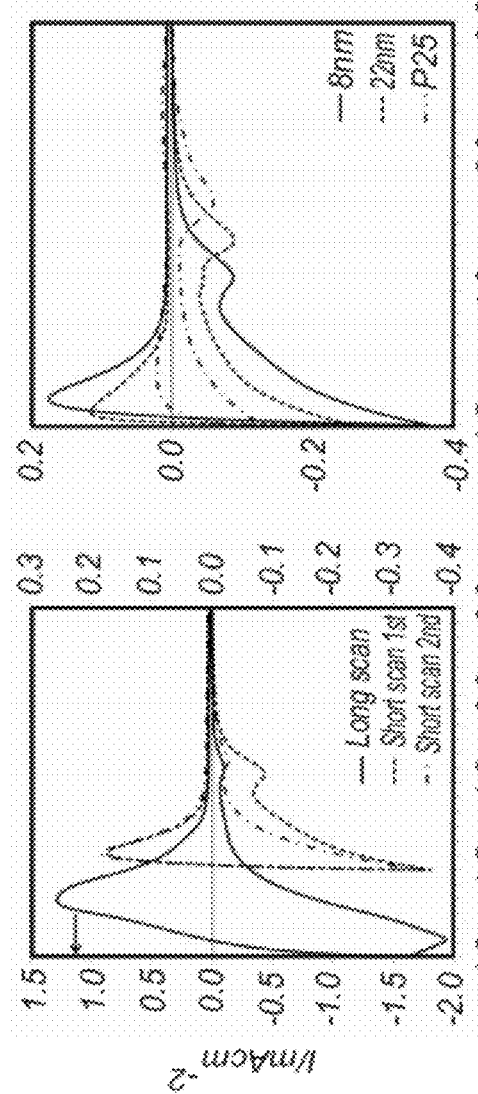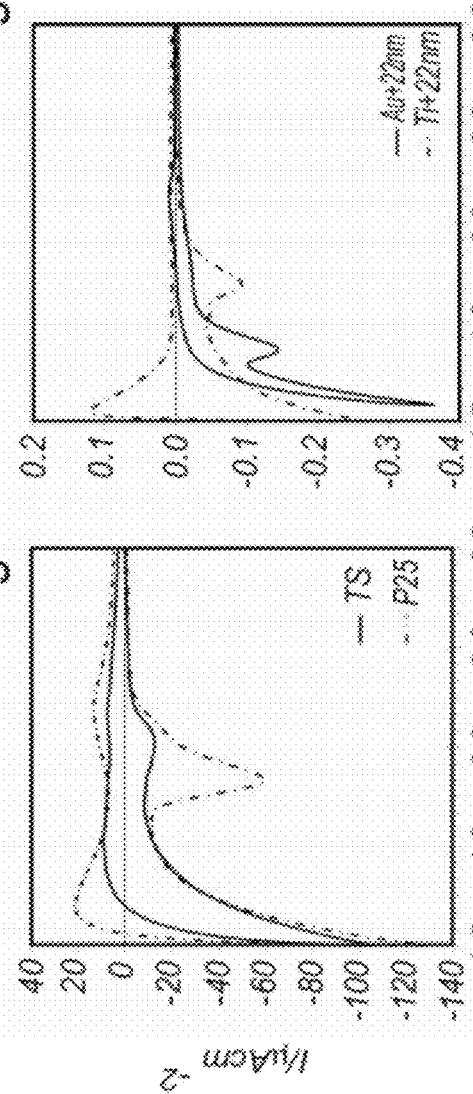
Fig. 3a  Fig. 3b  Fig. 3c  Fig. 3d

BIOCOMPATIBLE COMPONENT

RELATED DOCUMENTS

This application claims the benefit of priority of U.S. provisional application Ser. No. 61/484,951, filed May 11, 2011 and European application Ser. No. 11165686.4, filed May 11, 2011, which are herein incorporated by reference for all purposes.

FIELD OF THE INVENTION

The present invention relates to the field of biocompatible components intended for contact with living cells or tissue, in particular implants intended for implantation into living tissue.

BACKGROUND OF THE INVENTION

Dental implants are medical devices used to restore the function entailed with the loss of one or several teeth. To obtain successful function over long periods, the dental implants must be sufficiently anchored in the bone to withstand the forces induced by for example chewing. Two important factors for obtaining high anchorage strength are i) the chemical composition of the material and ii) the implant design at all length scales. Topographical features on different length scales induce for example nucleation sites for collagen and minerals, cell attachment and biomechanical stimulation necessary to prevent bone resorption and eventually to gain bone.

Dental implants commonly used today are made of titanium or titanium alloys with a screw shaped design and a rough surface.

There are to date several methods for treating metallic implants such as dental titanium implants in order to obtain a better attachment of the implant, and thus improved osseointegration. Some of these involve altering the morphology of the implant, for example by creating irregularities on the implant surface in order to increase the surface roughness in comparison to an untreated surface. It is believed that an increased surface roughness, which gives a larger contact and attachment area between the implant and the bone tissue, provides a better mechanical retention and strength between implant and bone. It is well-known within the art that a surface roughness can be provided by, for example, plasma spraying, blasting or acid etching.

Furthermore, it is known that osteoblasts, i.e, bone-forming cells, sense and react to multiple chemical and physical features of the underlying surface. Formation of bone at an implant surface requires the differentiation of precursor cells into secretory osteoblasts to produce unmineralised extracellular matrix (ECM), and the subsequent calcification of this matrix, as described in for instance Anselme K, Osteoblast adhesion on biomaterials, Biomaterials 21, 667-681 (2000).

Alteration of the chemical properties of the implant surface has frequently been used for achieving a better attachment of the implant to the bone tissue. Several methods involve the application of a layer of ceramic material, such as hydroxyapatite, on the implant surface in order to improve the bonding of the implant to bone since hydroxyapatite is chemically related to bone.

A common disadvantage with coatings comprising hydroxyapatite is, however, that they may be brittle and may flake or break off from the implant surface due to a stronger bond being formed between the bone and coating than between the coating and the implant, which may lead to an ultimate failure of the implant. Regarding the use of protein coatings, which have also been proposed, there are additional aspects to consider. Due to the chemical nature of proteins, a surface having a protein coating may require specific sterilization and storage conditions in order to maintain its biological activity. In addition, host tissue response (e.g. immunological response) to biomolecules such as proteins may be unpredictable.

Although various physical and chemical properties of implant surfaces are generally considered decisive factors for the biocompatibility of materials, the mechanism of new bone formation is still not known on a molecular level.

In brief, although there are many existing techniques for improving the osseointegration of an implant, there is a need for implants which offer further improved characteristics with respect to osseointegration and formation of a strong bone-implant attachment.

SUMMARY OF THE INVENTION

It is an object of the present invention to at least partly overcome problems of known implants associated with the formation of new tissue, in particular bone and/or osseointegration, and to provide a biocompatible component, e.g. part of a dental implant, which offers an improved tissue-implant attachment.

According to a first aspect of the invention, this and other objects are achieved by a biocompatible component having a surface intended for contact with living tissue, wherein the surface comprises particles of metal oxide, said particles having an average particle size of less than 100 nm. In preferred embodiments of the invention, the particles have an average particle size of less than 25 nm.

The present inventor found that by providing metal oxide particles of nanometer size on the surface of a biocompatible component, the bioactivity of the biocompatible component was increased in that it induced earlier apatite nucleation in vitro compared to a reference.

Upon implantation of an implant into the body of a patient, the implant surface comes into contact with e.g. blood. Ions present in the blood are attracted to the implant surface and start to form small hydroxyapatite crystals, a process called nucleation. The hydroxyapatite crystals subsequently contribute to the attraction of proteins and cells, such as osteoblasts, to the implant surface and the establishment of a tissue-implant bond. It is believed that the present biocompatible component will induce early hydroxyapatite nucleation in vivo and thus promote the osseointegration process, by enhancing the rate of tissue generation. It was observed that when immersed in simulated body fluid, biocompatible components according to embodiments of the invention within 12 h had induced the formation of apatite crystals having a Ca/P ratio of 1.7, which is the same as that of natural hydroxyapatite present in bone.

By applying a thin, relatively homogeneous layer of nanoparticles onto the surface of the biocompatible component, different surface properties are obtained compared to when applying a non-particular layer or coating of the same chemical composition and crystallinity for which bulk material properties are more dominating. It has for example been shown that small nanoparticles have higher surface charge compared to larger analogs (Zareen Abbas, Christophe Labbez, Sture Nordholm, and Elisabet Ahlberg., J. Phys. Chem. C 2008, 112, 5715-5723). It is believed that this may influence the apatite formation as well as adsorption of proteins and cells onto a surface coated with such particles.

The nano-sized particles of metal oxide may provide a nanoporous layer on the surface of the biocompatible component. The particles may be closed packed together on the surface, resulting in a layer with an inherent porosity ranging from 0.225*R for monolayers or from 0.732*R for multilayers, respectively, R being the radius of the nanoparticles. A multilayer, i.e. a layer comprising more than one particle in a direction normal to the surface in which the particles are present, may have higher porosity due to mismatch in the packing of the nanoparticles, which are substantially spherical. The porous nature of the layers result in a larger developed interfacial area compared to a surface without the nanoparticles. Moreover, the nanoparticles also provide a larger electrochemically active surface area, since an electrolyte can penetrate into the porous structure. Thus, the nanoparticle structure, which forms the external surface of the component, is more reactive and may have different electronic properties compared to a surface without the particles, or a surface having a coating of particles of larger size than the particles used in the present invention. It has also been found that the electronic properties of an oxide film covering a bone implant surface have larger effects on the cellular attachment and apatite nucleation than a small change in topography and that a less insulating oxide film may be preferable for titanium dental implants. Furthermore, a layer of particles as used in embodiments of the present invention may have such small porosity that it does not allow bacteria to penetrate into and/or accumulate within the layer.

Furthermore, it is believed that the high number of energy states in the band gap found for the surface comprising the nanoparticles may be beneficial for adsorption of redox active proteins such as fibrinogen.

In embodiments of the invention, the particles have a particle size distribution, taken as the ratio between the full width at half maximum (FWHM) divided by the mean particle size, obtained using electrospray-scanning mobility particle sizer (ES-SMPS), of up to 45%, preferably 40%, and more preferably up to 35%. Hence, as an example, for particles of average size of 10 nm, the individual particle size would be 10±4.5 nm, preferably 10±4.0 nm and more preferably 10+3.5 nm. As a result of the narrow particle size distribution, a smooth surface structure of particles is obtained having a corrugation following the sizes of the individual particles.

Typically the particles have a generally spherical shape.

In embodiments of the invention, the metal oxide is at least partly crystalline. Said metal oxide typically comprises titanium dioxide. In preferred embodiments, the predominant form of said titanium dioxide is anatase. For example, said titanium oxide may consist mainly of anatase (at least 50% anatase).

However, also other metal oxides may be used, typically in combination with titanium dioxide. In embodiments of the invention, the particles may comprise i) particles consisting essentially of titanium dioxide, and optionally also ii) particles consisting essentially of an oxide of one or more of zirconium, hafnium, vanadium, niobium, tantalum, cobalt and iridium, oxides of zirconium and/or iridium being particularly advantageous. Mixing titanium particles with particles of one or more of the above oxides, various properties of the resulting layer may be obtained e.g. with respect to colour, strength and/or electronic properties. For example, in combination with particles of titanium dioxide, particles of iridium oxide may be used to enhance the electronic properties of the layer.

In embodiments of the invention, the particles of metal oxide form a layer on at least a part of the surface of the biocompatible component. Thus, since the surface of the biocompatible component is intended for contact with living tissue, the particles are intended to be in contact with living tissue, in particular bone.

In embodiments of the invention, said layer formed by said particles may have a thickness in the range of from 8 nm to about 1 µm, typically from 50 nm to 500 nm, for example from 100 nm to 400 nm. Thin layers are advantageous because of better adherence to the substrate surface. Also, in the case of a sintered layer (see below) of particles, such thin layers may have higher strength than thicker layers. Said layer may be a monolayer of said particles.

Thus, the lower limit of layer thickness is about the same as the size of the particles. A thin layer of nano-sized particles will reduce the surface roughness on the submicrometer level, while preserving the surface roughness on a larger scale (blasting level). This is important for the long term osseointegration of an implant.

The layer may be a continuous layer of said particles, which layer may cover at least part of said surface. By continuous layer is meant a coherent layer forming a single area. Contrary to a continuous layer, a discontinuous layer would be formed of multiple separate layer areas. In embodiments of the invention, the particles may form a layer which completely covers the surface of the biocompatible component.

In embodiments of the invention, the particles are homogeneously distributed throughout said layer.

In embodiments of the invention, the particles may be sintered. Careful sintering of a layer of the nano-sized particles may improve the attachment of the particles to the substrate. Sintering of the particles may result in a ceramic or ceramic-like layer. However, the particles may also be non-sintered.

In embodiments of the invention, said surface has a relative active surface area, $A_{aa}$ (electrochemically active surface area) of at least 1.5, preferably at least 1.8, compared to a corresponding biocompatible component which lacks the particles and has a surface covered by native metal oxide. The increased active surface area results in a surface that is more reactive, and therefore may adsorb ions to a greater extent and/or enhance the rate of apatite precipitation.

In embodiments of the invention, the layer of said particles may have an average surface height $(S_a)$ in the range of from 5 nm to 70 nm, for example from 5 to 15 nm.

In embodiments of the invention, the biocompatible component comprises a substrate having said surface, wherein the substrate comprises a metallic material. Typically, the substrate comprises a metallic body formed of said metallic material. The metallic material may be selected from titanium, zirconium, hafnium, vanadium, niobium, tantalum, cobalt and iridium, and alloys thereof. A surface of the substrate that is in contact with said particles may comprise titanium oxide, in particular in embodiments where the substrate comprises or is formed of titanium. In such embodiments, the titanium oxide may be the native titanium oxide that naturally and instantaneously forms on a titanium surface upon contact with oxygen, e.g. in air. In embodiments where the substrate comprises or is formed of another metallic material mentioned above, a surface thereof that is in contact with said particles typically comprises a native oxide of the respective metal mentioned above.

In other embodiments of the invention, the substrate may comprise a non-metallic material, such as a biocompatible ceramic material, for example zirconia, or a biocompatible polymeric material. Suitable materials are known to those skilled in the art. In such embodiments, the substrate may be formed of a ceramic body, or of a body of polymeric material.

The biocompatible component according to the invention is typically intended for implantation into living tissue, in particular bone tissue. Alternatively, the component may be intended for implantation into soft tissue. For example, the biocompatible component may be a dental implant or a part thereof, such as a dental fixture. Alternatively, the biocompatible component may be an orthopedic implant or a part thereof.

Advantageously, the biocompatible component according to embodiments of the invention may induce nucleation of hydroxyapatite crystals within 12 hours when immersed in simulated body fluid.

In another aspect, the invention provides a method of producing a biocompatible component, comprising:
 a) providing a substrate having a surface;
 b) providing a dispersion of particles of metal oxide, which particles have an average particle size of less than 100 nm, which particles are dispersed in a solvent; and
 c) applying said dispersion of particles onto the surface of said substrate.

In the dispersion of step b), the particles may be completely dispersed. In such embodiments, in step c) each particle present in the dispersion will be applied on the surface individually. However, once applied onto the substrate surface, the particles are packed closely together to form a closely packed structure.

Typically, said particles have an average particle size of less than 25 nm.

The solvent may be an aqueous solvent, typically deionized water.

In embodiments of the invention, said dispersion of particles of metal oxide may be produced by:
 b-i) performing controlled hydrolysis of $TiCl_4$ to obtain a colloid dispersion; and
 b-ii) performing dialysis of said colloidal dispersion.

Step b-i) is typically performed by slow, preferably dropwise, addition of $TiCl_4$ to deionized water. The temperature of the $TiCl_4$ may be below 0° C., typically below −10° C., and the temperature of said water may be in the range of 0° C. to 5° C., preferably 0° C. under stirring.

The dispersion may be applied on the substrate by any suitable method, including spin coating, spray coating, dipping, immersion, sol-gel coating, electrophoretic deposition, etc.

In embodiments of the invention, the method further comprises allowing said solvent to evaporate after application of said dispersion.

Optionally, the method may further comprise the step of sintering said particles. In embodiments of the invention, a two step procedure may also be used in which a first layer of said particles is applied and sintered, and followed by application of further particles of metal oxide as described herein, which are not sintered. Thus, the benefits of both sintered and of non-sintered particles may be obtained.

The substrate may typically comprise a metal selected from titanium, zirconium, hafnium, vanadium, niobium, tantalum, cobalt and iridium, and alloys thereof, and preferably comprises titanium or an alloy thereof. The surface of the substrate may comprise a native metal oxide, such as native titanium oxide in the case of a titanium substrate.

In embodiments of the invention the surface of the substrate may be subjected to a roughening surface treatment prior to step c). Examples of roughening treatment include abrasive blasting and chemical etching. Alternatively, the substrate may be turned, or subjected to a non-roughening treatment, such as polishing.

It is noted that the invention relates to all possible combinations of features recited in the claims.

BRIEF DESCRIPTION OF THE DRAWINGS

FIG. 3 shows voltammograms obtained from cyclic voltammetry performed on surfaces comprising nanosized $TiO_2$ particles and a reference surface (TS).

DETAILED DESCRIPTION OF THE INVENTION

EXAMPLE 1

Figure 1:
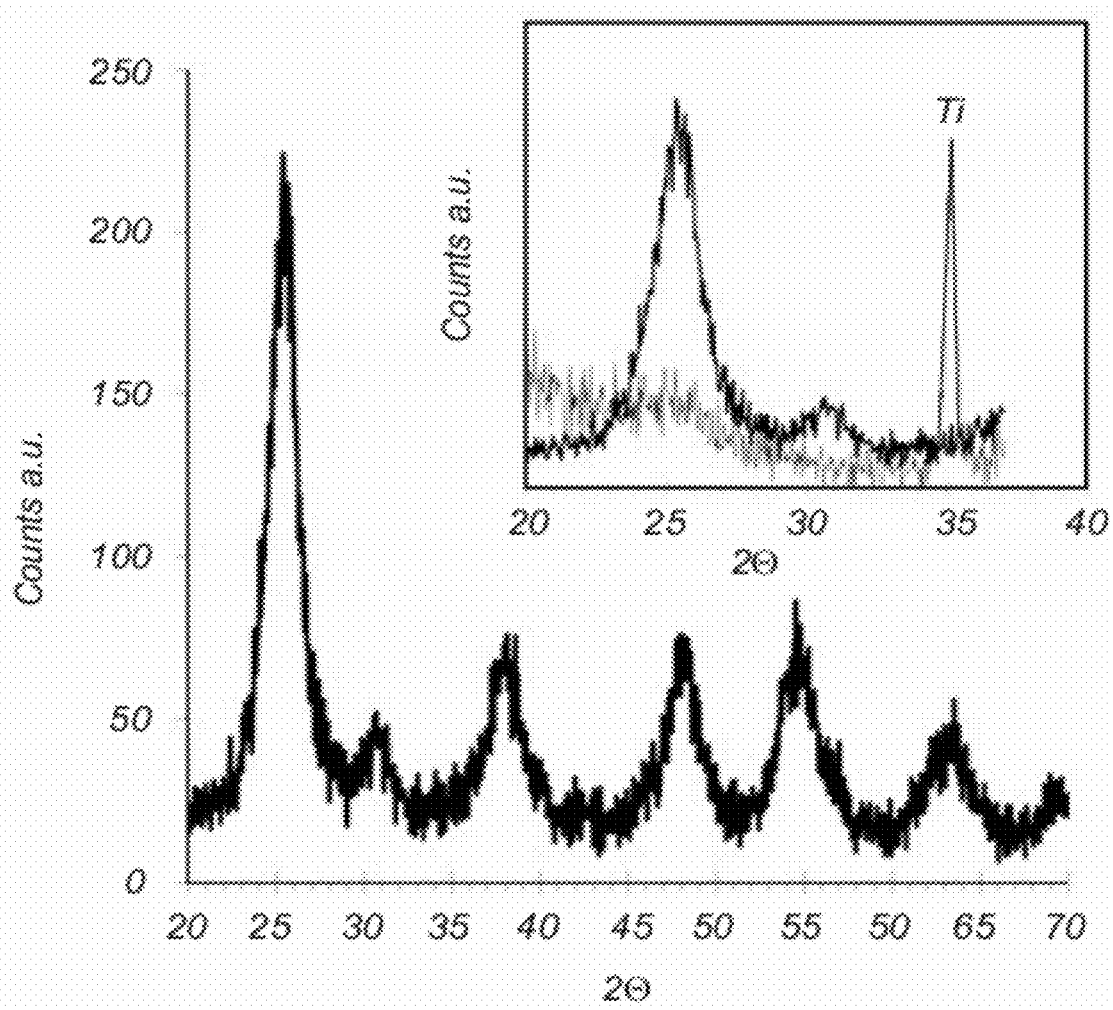
FIG. 1 shows the X-ray diffraction of $TiO_2$ nanoparticles according to embodiments of the invention.

Preparation and Characterization of Particle-containing Surfaces 1.1 Sample Preparation and Characterization
1.1.1 Sample Preparation Titanium dioxide ($TiO_2$) nanoparticles were synthesized by controlled hydrolysis of $TiCl_4$ to obtain clean surfaces of the particles. $TiO_2$ particles of different sizes were obtained by synthesis at 0° C. but with dialysis and storage of the colloidal dispersions done at 0° C. for 8 nm and 20° C. for 22 nm sized particles.

In a typical synthesis, $TiCl_4$ (99%) was cooled at −16° C. and 5.2±0.05 ml of this solution was added dropwise to 200 ml of de-ionized (Milli-Q) water under vigorous stirring. The synthesis was mostly done using a 1:40 $TiCl_4$:$H_2O$ volume ratio with a resulting $TiO_2$ concentration of 18 g/l. $TiO_2$ particles of different sizes are obtained by adjusting the reaction temperature, dialysis time/temperature and storage time/temperature. The dialysis step is important to avoid agglomeration and the resulting suspensions consist mainly of single nanoparticles. Details of the synthesis can be found in Z. Abbas, J. Perez Holmberg, A.-K. Hellström, M. Hagström, J. Bergenholtz, M. Hassellöv and E. Ahlberg, *Colloids Surf. A: Physicochem. Eng. Aspects*, 2011, doi: 10.1016/j.colsurfa.2011.03.064. The synthesis results in a dispersion in which the particles are substantially monodisperse (Perez Holmberg, Z. Abbas, E. Ahlberg, M. Hassellöv and J. Bergenholtz, *J. Phys. Chem. C*, 2011, accepted for publication).

Commercial $TiO_2$ particles (Degussa P25), with an individual particle size in the range of 30-80 nm and 4:1 ratio of anatase to rutile, were carefully washed to remove organic surface species and treated in ultrasonic bath to obtain a dispersed solution. However, dynamic light scattering showed the existence of larger aggregates and it was not possible to fully disperse the system. The particles were spin coated onto Ti (Grade 4 discs with a turned surface, diameter 1.1 cm,) or Au disks (polished with SiC paper (4000), diameter 0.6 cm) in several steps. After spin coating, the samples were rinsed with deionized water and left to dry before use. As a complement to the nanoparticle-containing surfaces, the nanostructured TS+AT1 (turned surface treated sequentially with oxalic acid and hydrofluoric acid) surface was included in this study.

1.1.2 Determination of Particle Size Distribution

The particle size distributions of the synthesized $TiO_2$ nanoparticles can be obtained by the electrospray-scanning mobility particle sizer (ES-SMPS) method as described in Z. Abbas, J. Perez Holmberg, A.-K. Hellström, M. Hagström, J. Bergenholtz, M. Hassellöv and E. Ahlberg, *Colloids Surf. A: Physicochem. Eng. Aspects*, 2011, doi:10.1016/j.colsurfa.2011.03.064.

1.1.3 Surface Topography

High resolution SEM images were recorded using Leo Ultra 55 FEG SEM operated at 1 kV. Surface roughness analysis was performed by using Atomic Force Microscopy (AFM) (Nanoscope® Multimode IIIa, Digital Instruments). Tapping Mode AFM measurements were performed at three points per sample and at three different scan sizes, 10×10, 5×5, and 3×3 μm (scan frequency 0.8 Hz, 512 lines). The AFM data were imported into MeX® 19 (Alicona Imaging GmbH) software where roughness analysis and calculation of 3D-surface roughness parameters were performed. By using multiple scan sizes and by applying a Gaussian filter of different sizes in the MeX® software, information about topographical features ranging from 10 μm to 150 nm are received.

1.1.4 Surface Analysis

A Siemens D5000 powder diffractometer which utilizes CuKα radiation ($\lambda$=1.54056 Å) was used for identification of crystalline phases. X-ray diffraction was measured at different incidence angles in order to obtain information from different depth of the samples. For XPS analysis a Quantum 2000 ESCA Scanning Microscope, (Physical Electronics, USA) with an X-ray source of monochromatic AlKα was used.

1.1.5 Electrochemical Measurements

Cyclic voltammetry and impedance measurements were performed by using a Gamry Reference 600™ Potentiostat/Galvanostat/ZRA. The electro-chemical measurements were done in a specially designed three electrode cell used for stationary conditions. The sample is placed at the bottom of the cell with the turned surface towards the electrolyte. A large Pt counter electrode is concentrically placed around the sample to assure optimal current distribution and the reference electrode is place in the middle of the cell. This cell configuration is useful for all types of planar samples and shows good characteristics in impedance measurements. All potentials are referred to the Ag/AgCl (sat KCl, E=0.197 V vs. she) reference electrode. Electro-chemical impedance (EIS) measurements were performed in deaerated 0.5 M $H_2SO_4$ and a continuous low purge with $N_2$ gas was maintained during the impedance measurements. Impedance spectra were recorded at constant potential in the frequency range 1 kHz to 10 mHz, with 9 point/decade and an amplitude of 10 mV rms. The potential was stepped by 50 mV from +1 to −0.5 V with a waiting time of 300 s before the next spectra was recorded. Cyclic voltammetry was obtained in 0.1 M KOH using a sweep rate of 50 mVs$^{-1}$.

1.2. Surface Characterization Results
1.2.1 Particle Size Distribution

The particle size distributions obtained after 1 and 3 weeks of storage for dispersions stored at 0° C. and at room temperature are very similar. Previous analyses (Z Abbas, et al., *Colloids Surf. A: Physicochem. Eng. Aspects*, 2011, doi:10.1016/j.colsurfa.2011.03.064) have shown that $TiO_2$ colloidal nanoparticles with narrow size distribution can be obtained. The distribution was measured as the ratio between the full width at half maximum (FWHM) divided by the mean size and was found to be 35-40%.

1.2.2 XRD and XPS

FIG. 1 shows x-ray diffraction of the nanoparticles in powder form obtained from suspensions containing 8 or 22 nm particles. The particles were dried at 120° C. for 16 hours prior to analysis. The main phase is anatase but with a small contribution from brookite as shown by the reflection at 2θ=30.8°. The broad diffraction peaks indicate that the particles consist of smaller crystallites (~4 nm) and growth studies have shown that the particles are formed by slow aggregation of initially formed precipitates of this size. In the inset of FIG. 1, the diffraction pattern for the particles attached to titanium is shown. Since the nanoparticle layer is thin, the signal is very weak but the main anatase peak can be observed. This shows that the phase of the particles remains after deposition and drying. The P25 particles attached to titanium show typical diffraction pattern with a ratio between anatase and rutile of ~4/1. For the TS+AT1 modification, no diffraction peaks from the oxide can be observed, which indicates that the precipitated layer is amorphous or too thin to be detected.

XPS analysis performed on the nanoparticle layers shows pure $TiO_2$ with traces of chloride. No signal for Ti metal was observed, which indicates that the films fully cover the surface. Lower valent titanium ions were not observed. The carbon signal is similar for all samples and is related to surface contamination.

1.2.3 Surface Topography Results

Figures 2A, 2B, 2C:
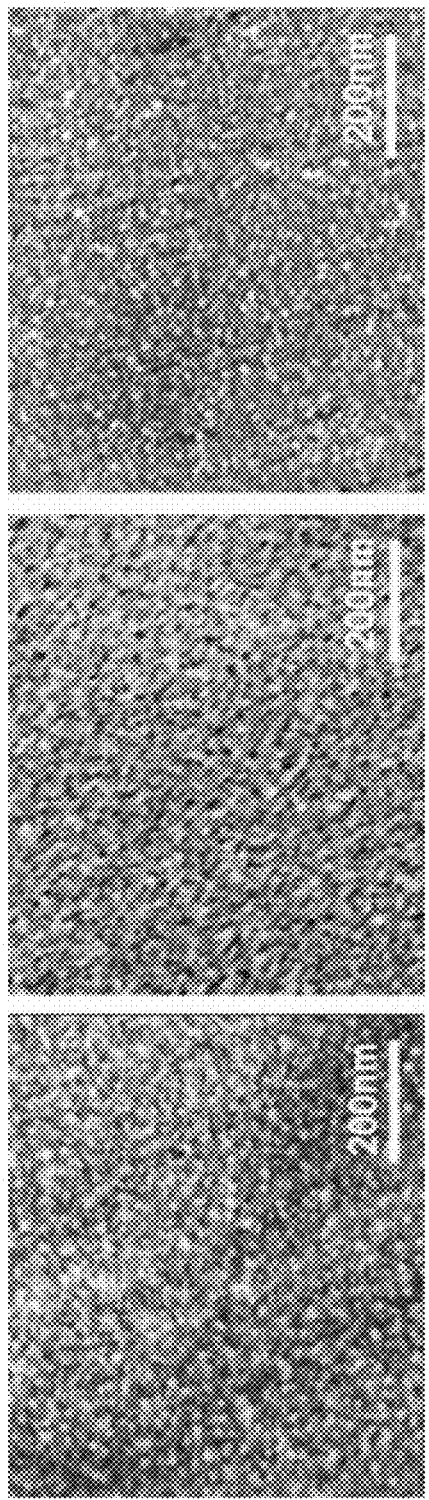
FIG. 2a-c show high resolution SEM images of surfaces comprising $TiO_2$ particles of 8 nm (FIG. 2a) and 22 nm (FIG. 2b,c), commercial $TiO_2$ particles (FIG. 2d) and a double etched surface without particles (FIG. 2e).
Figure 2E:
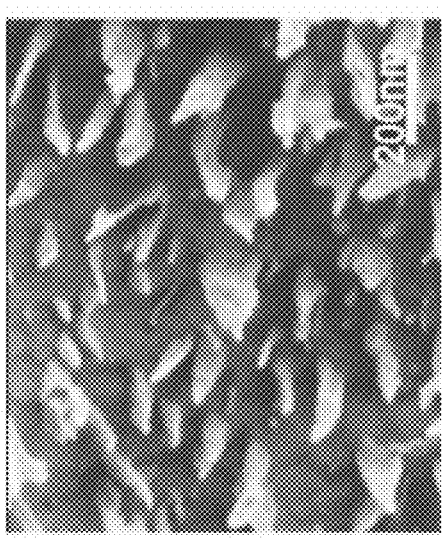
Figure 2D:
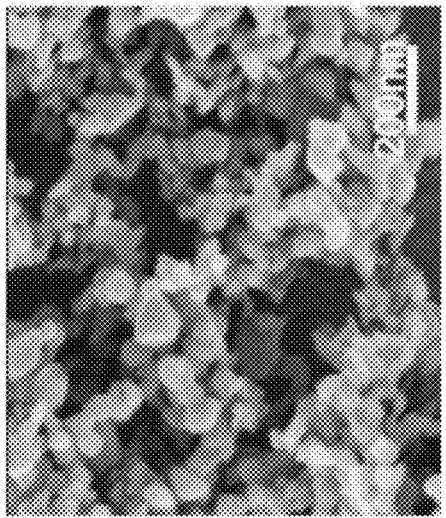

FIG. 2 shows high-resolution SEM images of surfaces comprising respectively 8 nm (TS+8 nm, FIG. 2a) or 22 nm (TS+22 nm, FIG. 2b; Au+22 nm, FIG. 2c) $TiO_2$ particles. All three surfaces look fairly smooth. From the SEM images of these surfaces it seems like the underlying substrate is fully covered. This is not the case for the two other modifications used in the present work. The suspension of P25 contained agglomerates of particles and these were transferred to the Ti surface during the spin coating procedure. As a result the surface roughness is high but in between the turned surface is visible, FIG. 2d. For the TS+AT1 surface etched in oxalic acid and hydrofluoric acid sequentially, rather large precipitates form with a very thin oxide layer in between. In contrast to the spherical nanoparticles, the precipitates on the TS+AT1 surface can be regarded as rods with a height of 0.45 μm (determined from the average of maximum height of 5 peaks and valleys, $S_{10z}$), see FIG. 2e.

Topographical analysis of the surfaces was performed by AFM analysis using overlapping scan sizes and Gaussian filter of different sizes to obtain information of surface features in the range of 10 to 0.150 μm. The 3D-surface roughness parameters were calculated using the MeX® software and values for three different parameters are listed in Table 1.

TABLE 1

3-D surface roughness parameters determined by AFM.

| Sample | $S_a$ (nm) | | $S_{dq}$ | | $S_{dr}$ (%) | |
|---|---|---|---|---|---|---|
| | average | stdev | average | stdev | average | stdev |
| TS (Ti) | 11.6 | 0.67 | 0.26 | 0.09 | 3.51 | 2.06 |
| TS + 8 nm | 8.34 | — | 0.14 | — | 1.05 | — |
| TS + 22 nm | 10.6 | 1.4 | 0.16 | 0.01 | 1.32 | 0.20 |
| TS + P25 | 63.3 | 9.2 | 1.73 | 0.26 | 109.3 | 24.5 |
| TS + AT1 | 41.8 | 6.2 | 0.89 | 0.23 | 38.3 | 19.2 |
| Au | 13.9 | — | 0.24 | — | 2.68 | — |
| Au + 22 nm | 9.02 | 1.8 | 0.14 | 0.02 | 1.00 | 0.70 |

$S_a$ = Average height of surface, $S_{dr}$ = Developed interfacial area, $S_{dq}$ = Root-mean-square of surface slope. Data from 10 × 10 μm scan size a Gaussian filter of 20% of the horizontal width (1.996 μm).

The $S_a$ value (average height) is significantly larger for the surfaces TS+P25 and TS+AT1 than for the surfaces comprising nanoparticles and the turned surface. Both these surface treatments induced additional surface structures on top of the turned surface without fully covering it, FIG. 2d-e. The layers of 8 and 22 nm particles respectively completely covered the turned surface with particles, which in turn caused a decrease in surface roughness since the turning tracks are covered, see FIG. 2a-b and Table 1. The same trend is observed for the gold substrate (FIG. 2c), where the $S_a$ value decreases after applying a layer of 22 nm particles. There is only a slight difference between the $S_a$ values for the TS+8 nm and TS+22 nm surfaces, but the lower value obtained for the smaller particles indicates that the curvature of the particles are reflected in the surface roughness. The root mean square of the slope ($S_{dq}$) has been shown to correlate with the interface shear strength and is thus an important parameter to investigate for dental implant applications. From a biomechanical point of view a large $S_{dq}$ value may be desired. The trend in $S_{dr}$ (developed interfacial area) values follows the same trend as the $S_a$ and $S_{dq}$ values with the smallest values obtained for the surfaces comprising nanoparticles.

1.3. Electrochemical Characterization 1.3.1 Cyclic Voltammetry (CV)

In FIG. 3 examples of voltammograms are shown to illustrate the influence of scan range and number of scans for one type of electrodes (FIG. 3a), different particle sizes (FIG. 3b), partially coated electrodes (FIG. 3c) and different substrates (FIG. 3d). The general features of the voltammograms obtained with Ti as substrate are the same with a symmetrical process at the most negative potentials and a peak at less negative potentials. The process observed at the most negative potentials has been attributed to charge accumulation in the conduction band, reaction (1), or filling traps just below the conduction band, reaction (2). In both cases adsorption of protons takes place to obtain charge balance in acid solution.

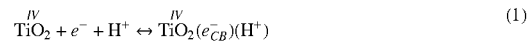

$$\overset{IV}{Ti}O_2 + e^- + H^+ \leftrightarrow \overset{IV}{Ti}O_2(e_{CB}^-)(H^+) \quad (1)$$

$$\overset{IV}{Ti}O_2 + e^- + H^+ \leftrightarrow \overset{III}{Ti}O_2(H^+) \quad (2)$$

In alkaline solutions the electrolyte cation is probably the charge balancing species, i.e. adsorption of K+ in the present case. The peak at less negative potentials has been attributed to filling of surface states below the conduction band, i.e. reduction of Ti(IV) to Ti(III) according to (2). For reaction (2) the formation of TiO(OH) is also possible in alkaline solution. Alternatively, the peak at less negative potentials can be attributed to trap states at the grain boundaries in the film. Usually, the current at the most negative potentials increases exponentially and eventually hydrogen evolution takes place by reduction of water. The symmetry between cathodic and anodic charge observed for the nanoparticle covered electrodes, TS+8 nm and TS+22 nm, indicates that Faradaic processes are not involved if the potential is limited to −1.8 V. Polarising to more negative potentials results in further increase in the current due to hydrogen evolution (not shown). In contrast to other studies on nanoparticle covered electrodes the current goes through a maximum on the negative going scan, before hydrogen evolution sets in. The reason for this is not known but may be related to complete filling of energy levels just below the conduction band. The peak at less negative potentials has been attributed to filling of surface states or trap states at the grain boundaries in the film as mentioned above. In the present study, the films are not sintered and the amount of grain boundaries is expected to be low and therefore the peak is most likely due to surface states. The positive potential limit was 0 V but this was not sufficient to completely emptying the surface bands filled during the negative going scan. This is evident from the much smaller peak observed on subsequent sweeps, FIG. 3a. The peak potential shifts depending on the coating with the most negative peak potential for the TS+8 nm electrode followed by the TS+22 nm and TS+P25 surfaces, FIG. 3b and Table 2. Also the current for the process at more negative potentials depend on the type of particles, FIG. 3b, and has been related to the active surface area of nanoparticle films, indicating that the active surface area increases with decreasing particle size. For the native oxide always present on titanium metal, the reduction peak appears at less negative potentials (−0.89 V) compared with the particle covered electrodes and the redox process shows some reversibility with an oxidation peak at −0.81 V. Some reversibility in the redox process at these potentials is also observed for the TS+P25 electrode, FIG. 3c. The total charge for the naturally formed oxide is lower than for TS+P25, which is expected since the available surface area will be larger for the nanoparticle film of P25. A close look at the voltammogram for TS+P25 indicates that there is a contribution from the uncovered surface with naturally formed oxide (shown as a shoulder of the peak). This is in agreement with the SEM image in FIG. 2d, where the uncovered surface is visible in the porous structure. The process at more negative potential is however the same and differs only in the reversibility with higher anodic charge for the TS+P25 electrode. The reversibility of this process is higher for the TS+8 nm and TS+22 nm electrodes compared to TS+P25 and the turned surfaces and is probably related to the smaller particle sizes and well defined surfaces. The lack of reversibility can be due to Faradaic processes and that is probably the case for the gold electrode covered with 22 nm $TiO_2$ particles, Au+22 nm. The reduction peak is closer to the conduction band and hydrogen evolution is probably taking place at more negative potentials since no oxidation peak is observed, FIG. 3d. However, a small oxidation peak is observed at −0.82 V, in close agreement with the peak observed for the Ti-coated electrodes. This peak is associated with emptying of energy states on the surface of the $TiO_2$ particles.

Based on the voltammetric response and assuming that no Faradaic processes occur, the density of states (DOS) in the band gap and the electron density can be determined using Eqn. 3.

$$g_0(-eV) = -\left(\frac{I}{eLAv}\right)(eV) \quad (3)$$

where $g_0(-eE)$ is the first estimate of the DOS in the band gap valid at zero Kelvin. E is the electrode potential, L the thickness of the layer, e the elemental charge, A the surface area and v the sweep rate. The experimental data show two types of states, one associated with the exponential tail of the conduction band, $g_{tail}(-eE)$, at the most negative potentials, and states in the band gap with a Gaussian-like distribution, $g_{gauss}(-eE)$, see Eqns. 4 and 5.

$$g_{tail}(-eE) = g_{tail,BE} \exp[-\alpha FE/RT] \quad (4)$$

where $g_{tail,BE}$ is the DOS at the edge of the conduction band and α is related to extension of the tail into the band gap. The Gaussian distribution is given in Eqn. 5.

$$g_{gauss}(-eV) = g_{gauss,sat} \cdot \frac{\exp[-(E - E_p)^2/2\sigma^2]}{\sigma\sqrt{2\pi}} \quad (5)$$

where $g_{tail,BE}$ corresponds to the complete filling of the states in the band gap, $E_p$ is the peak potential and σ the standard deviation about the peak potential. An attempt was made to fit experimental data to these equations but the states in the band gap deviates from a Gaussian distribution and reliable values could not be obtained. For porous nanostructured films the charge associated with the exponential increase has previously been shown to be proportional to the interfacial area. Since the exact thicknesses of the particle layers are not known, the values extracted from the exponential term can only be used to calculate the interfacial area normalized with the area of the reference surface (lacking particles), Table 2. Comparing these values with the developed interfacial area, $S_{dr}$, shows that even though P25 has the largest $S_{dr}$ value the active area is only slightly higher than for the turned surface. In contrast, the smooth appearance of the TS+8 nm and TS+22 nm surfaces yields higher interfacial area with the largest one obtained for the smallest nanoparticles. The lack of agreement originates from the fact that $S_{dr}$ represents the physical (passive) area while the interfacial (active) area is created in contact with the electrolyte.

1.3.2 Electrochemical Impedance Spectroscopy (EIS)

Impedance data were measured as a function of potential in the frequency range 100 kHz to 10 mHz with an amplitude of 10 mV rms. The impedance data were fitted by using equivalent circuits consisting of one or two time constants in series with the solution resistance ($R_{sol}$). Each time constant consists of a constant phase element (CPE) in parallel with a resistance related to the oxide. It has been demonstrated that for lateral distribution of time constants the solution resistance is included in the calculations, while for a distribution of time constant perpendicular to the surface it can be omitted. For the system studied here, where a porous oxide is formed and electrolyte can penetrate most of the porous layer, distribution of time constants occurs laterally due to the porosity of the surface and the effective capacitance has therefore been calculated using Eqn. 6, $$C = \left[Q \cdot \left(\frac{1}{R_{sol}} + \frac{1}{R_{film}}\right)^{\alpha-1}\right]^{\frac{1}{\alpha}} \quad (6)$$

where $R_{sol}$ is the solution resistance, $R_{film}$ is related to the oxide film resistance and α is the dispersion factor for the CPE element. The effective capacitance was used to estimate the electric properties of the semiconducting titanium dioxide layer using the well known Mott-Schottky relationship, Eqn. 7:

$$\frac{1}{C_{sc}^2} = \left(\frac{2}{\varepsilon_r\varepsilon_0 eN_d}\right)\left(E - E_{fb} - \frac{kT}{e}\right) \quad (7)$$

where $C_{sc}$ is the space charge capacitance, $\varepsilon_r$ the dielectric constant of $TiO_2$, $\varepsilon_o$ the dielectric constant of vacuum, $N_d$ the number of charge carriers, e the charge of the electron, E the applied potential and $E_{fb}$ the flat band potential. Here it is assumed that the double layer capacitance is much higher than the space charge capacitance. According to Eqn. 7 a linear dependence is expected from which the number of charge carriers can be obtained from the slope and the flat band potential from the intercept.

Figure 4:
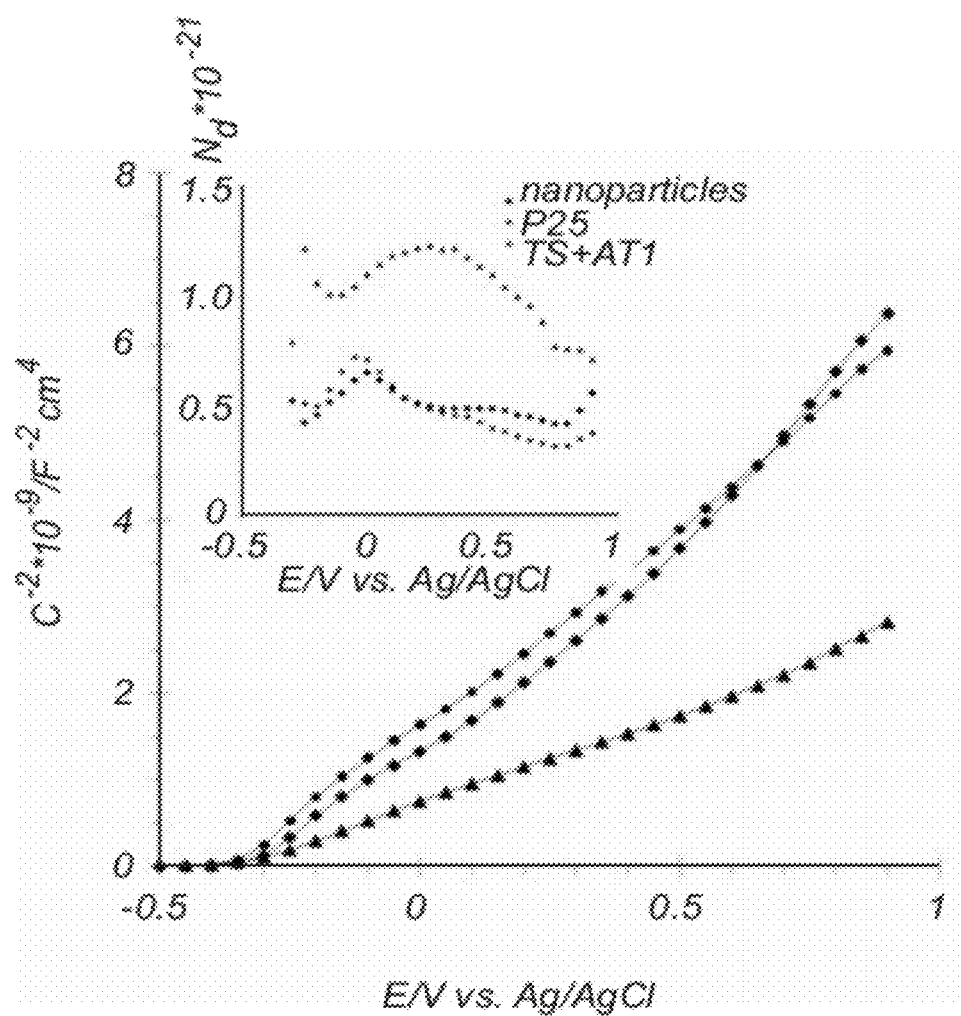
FIG. 4 shows Mott-Schottky plots for the different titanium (Ti) surfaces studied herein.

In FIG. 4, Mott-Schottky plots for the different surfaces are shown. For Ti surfaces comprising 8 and 22 nm particles the Mott-Schottky behaviour is the same and only one curve is shown in the graph. For these surfaces a linear Mott-Schottky relationship is found except close to the flat band potential, where a non-linear behaviour is observed for all surfaces. For the TS+P25 and TS+AT1 surfaces a change in the slope is observed at the most positive potentials. The number of charge carriers was calculated at each potential from the slope of the Mott-Schottky plot and is given in the inset to FIG. 4. Despite changes in the slope of the Mott- Schottky curves the number of charge carriers is fairly constant and the value for the most linear region is given in Table 2 below together with the flat band potential. The flat band potentials were similar for the different surfaces.

For the surface covered with P25 the slope increases significantly at potentials higher that 0.4 V, giving a lower donor density by a factor of 1.6. This line can be extrapolated to yield an apparent flat band potential close to 0 V. This value is the same as found for anodized layers on the same base material. Since the flat band potential is expected to be close to −0.35 V at the pH used in the present work, the apparent flat band potential is probably affected by surface states. Also in the case of anodized films a reduction peak is observed representing surface states with energy bands in the band gap.

Figure 5:
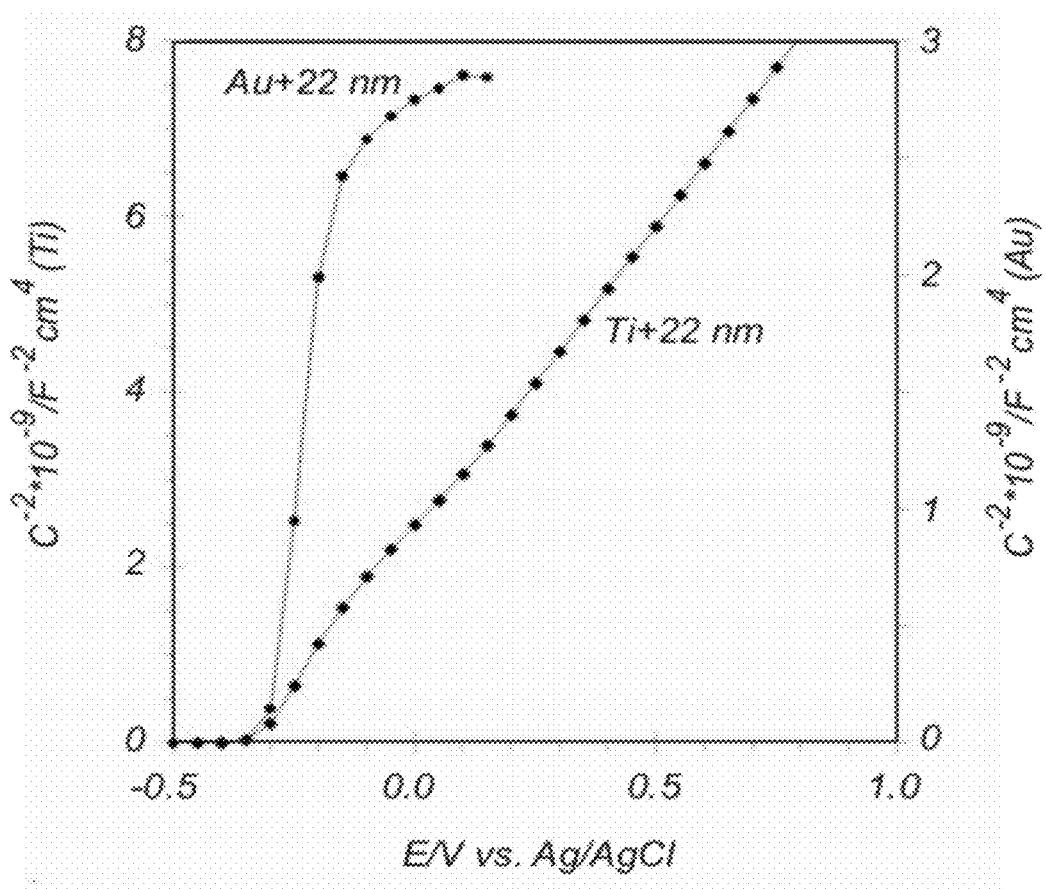
FIG. 5 shows Mott-Schottky plots for a gold surface comprising nanosized $TiO_2$ particles.

The Mott-Schottky plot for the Au+22 nm electrode looks different compared with the other electrodes, FIG. 5. In this case the capacitance was calculated from impedance values obtained at a constant frequency of 100 Hz. For comparison, the Mott-Schottky curve for the TS+22 nm electrode is also shown, with capacitance values calculated in the same way. Starting at positive potentials the capacitance is constant for the Au+22 nm surface, i.e. independent of potential. This capacitance is therefore related to the capacitance of the insulating oxide film. Close to the flat band potential the curve changes rapidly. By correcting for the oxide capacitance, the donor density and the flat band potential can be estimated, see Table 2 below. From the oxide capacitance value, the average oxide thickness can be calculated using Eqn. 8. A value of 28 nm was obtained, which indicates that only a monolayer of particles is attached to the surface in case of gold.

$$d = \frac{\varepsilon_0 \varepsilon_r A}{C} \quad (8)$$

where $\varepsilon_0$ is the dielectric permittivity of vacuum, $\varepsilon_r$ is the dielectric constant of $TiO_2$ (60), A is the electrode area and C the capacitance.

The number of charge carriers is much lower for the nanoparticles film on gold than for the same film on titanium. This indicates that the $TiO_2$ nanoparticles are interacting more closely with the thin oxide film on titanium than with the gold metal. As a consequence it might be concluded that the surface states observed in cyclic voltammetry originates not only from the particles but also from the interface between the particles and the native oxide film on Ti. For the TS+AT1 surface the number of charge carriers is higher than for the nanoparticle films and also higher than for the native oxide (TS), Table 2. One reason for the slightly higher conductivity could be the presence of titanium hydride in the metal phase. However, for blasted samples the conductivity for surface with the AT1 treatment were found to be lower than for the blasted sample (I. Mattisson and E. Ahlberg, *Appl. Surf. Sci.*, 2011, Accepted for publication).

Figure 6:
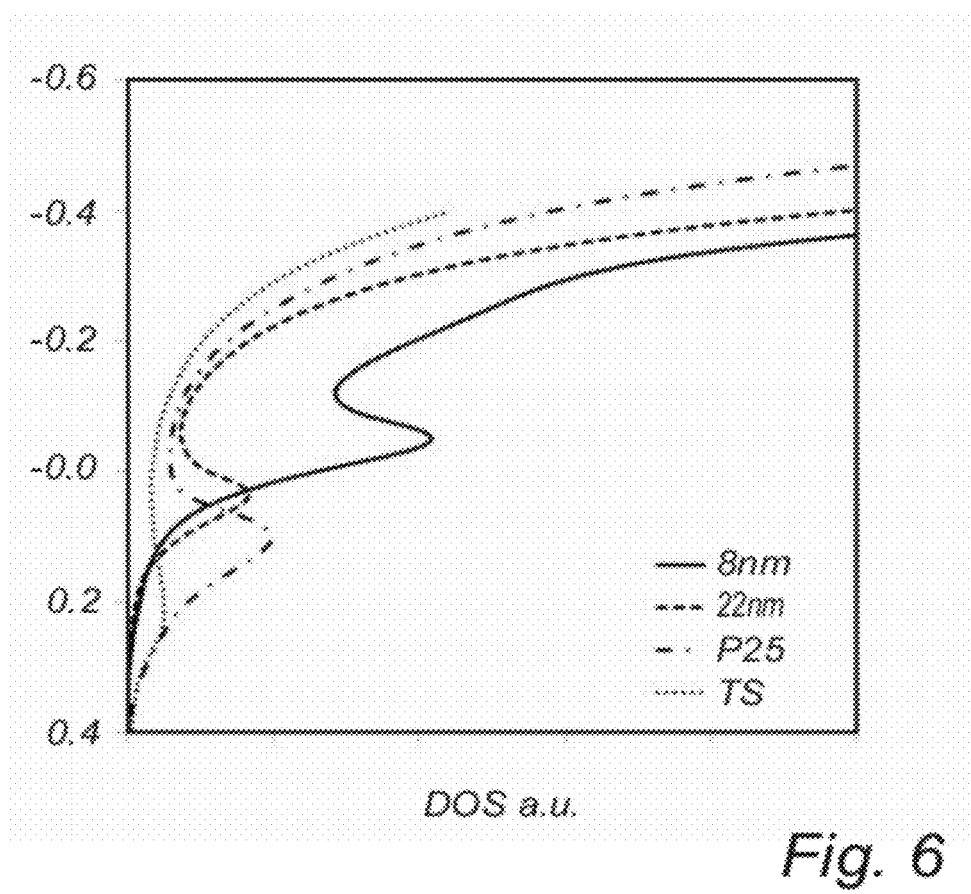
FIG. 6 shows the density of states (DOS) of surfaces comprising nanosized $TiO_2$ particles and a reference surface, as a function of potential with reference to the flat band potential.

The voltammetric measurements were made in alkaline solution and by using the experimentally determined flat band potentials obtained in acid solution and assuming a Nernstian pH shift, the flat band potential was calculated for pH 13, Efb=−1.1±0.1 V. In FIG. 6, the density of states (DOS) is plotted as a function of potential with reference to the flat band potential.

For the surface with 8 nm particles the maximum in DOS occurs at higher energies than the flat band potential, while for the other surfaces the maximum is close to $E_{fb}$ (TS+22 nm) and at positive potentials with respect to $E_{fb}$ (TS+P25 and TS). The location of the energy bands may be important for adsorption of bioactive compounds and in turn for the surface ability to function in-vivo. This will be further discussed below in relation to the result obtained after immersion in simulated body fluid.

TABLE 2

Peak potentials determined from CV, $E_{fb}$, and $N_d$ determined from EIS

| Sample | [a]$E_p$/V | [b]Rel. active area ($A_{aa}$) | [c]$E_{fb}$/V | [c]$N_d$ $10^{-19}$/ cm$^{-3}$ | [d]$N_d$ $10^{-19}/A_{aa}$ |
|---|---|---|---|---|---|
| TS | −0.89 | 1 | −0.35[d] | 84[d] | 84 |
| TS + 8 nm | −1.16 | 2.65 | −0.30 | 47 | 17.7 |
| TS + 22 nm | −1.09 | 1.77 | −0.30 | 47 | 26.6 |
| TS + P25 | −1.00 | 1.30 | −0.35 | 50 | 38.5 |
| TS + AT1 | −0.93 | 1.88 | −0.41 | 119 | 63.3 |
| Au + 22 nm | −1.27 | — | −0.33 | 0.13 | — |

[a]$E_p$ is determined in 0.1M KOH.
[b]Calculated on the exponential term for E = 0 − (−1.5) V.
[c]$E_{fb}$ and $N_d$ are determined in 0.5M $H_2SO_4$.
[d]From U. Pettersson, J. L. Löberg, A. S. Fredriksson and E. K. Ahlberg, *Biomaterials*, 2009, 30, 4471-4479, recalculating the value for $E_{fb}$ to the pH used in this study.

EXAMPLE 2

Evaluation of Surface Bioactivity 2.1. Sample Preparation 2.1.1 Immersion in Simulated Body Fluid (SBF)

The SBF solution was prepared at 37° C. according to the revised SBF recipe described in A. Oyane, H. M. Kim, T. Furuya, T. Kokubo, T. Miyazaki and T. Nakamura, *J. Biomech. Mater. Res. A*, 2003, 65, 188-195. The pH of the solution was set to 7.00±0.05 using 1 M NaOH and the prepared SBF solution was used fresh.

Samples prepared according to Example 1.1 above were individually immersed and mounted with the treated surface up-side-down in 40 ml SBF solution. 9 samples per category were immersed at 37.0° C. and 3 samples per category were evaluated after 12 h, 72 h and 1 week of immersion, respectively. X-ray diffraction (XRD) analysis was performed at one sample per category and immersion time to investigate the chemical composition of the sample. SEM (ESEM XL30, FEI Company) and energy-dispersive X-ray spectroscopy (EDX) (Apollo 14, EDAX) analysis were performed at 3 points per sample for all sample types to evaluate the amount and morphology of the formed apatite. SEM settings used were 10 kV, working distance 10 mm and analysis area 126×102 μm.

2.2 Results

The ability of the surfaces to induce apatite nucleation was evaluated by immersion samples in SBF solution for 12 h, 72 h and 1 week. The SBF solution contains ions with similar concentration as the human blood plasma and the recipe for SBF solutions can vary. In the present paper the revised SBF recipe presented by Oyano et al was used. The samples were mounted with the treated surface hanging up-side down to prevent gravitational precipitation.

The amount of apatite formed was measured by EDX. The apatite coverage (Θ) was calculated from the ratio of the titanium signal after and before immersion in SBF solution using Eqn. 9. It is assumed that apatite is the only precipitate formed during immersion.

$$\Theta = 1 - \left(\frac{Ti_{SBF}}{Ti}\right) \quad (9)$$

Figure 7:
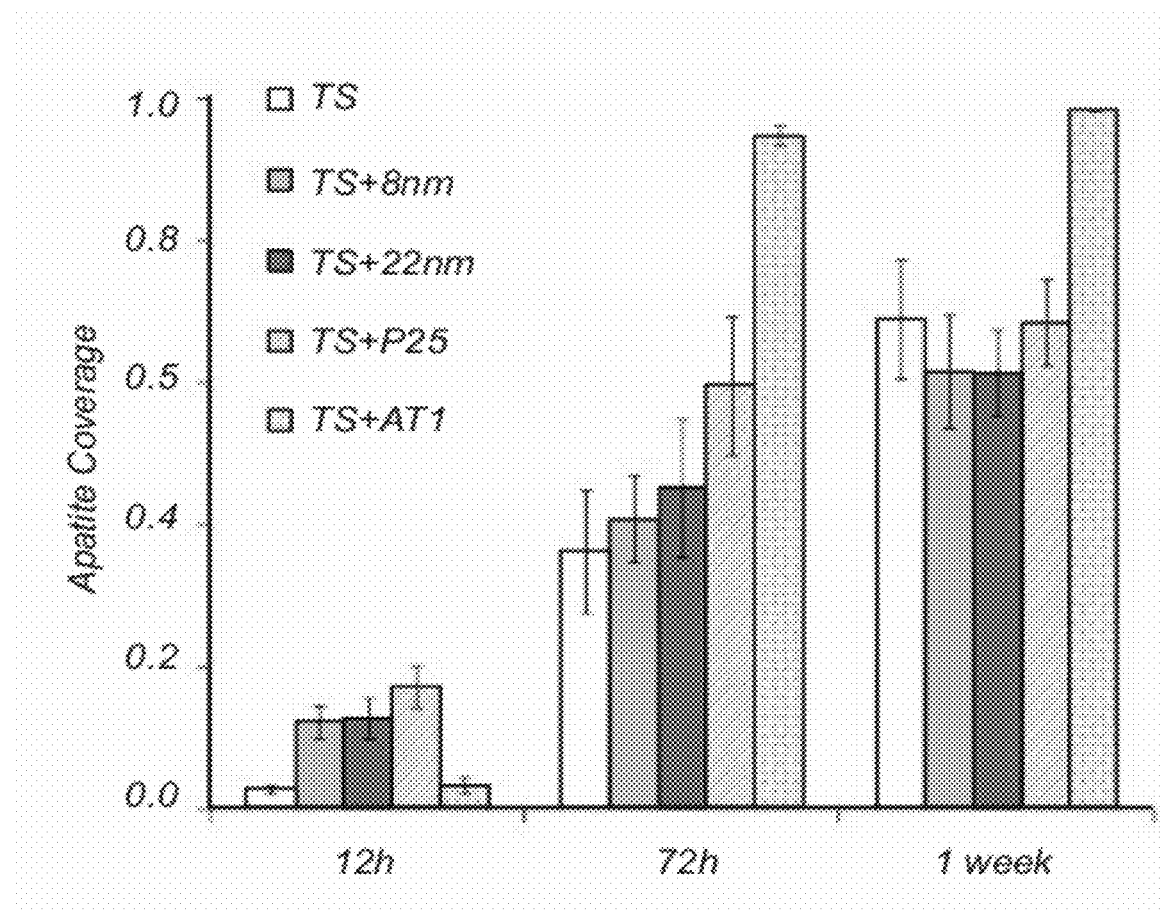
FIG. 7 is a graph showing the apatite coverage on five different surfaces after 12 hours, 72 hours and 1 week, respectively, of immersion in simulated body fluid.
Figure 8A:
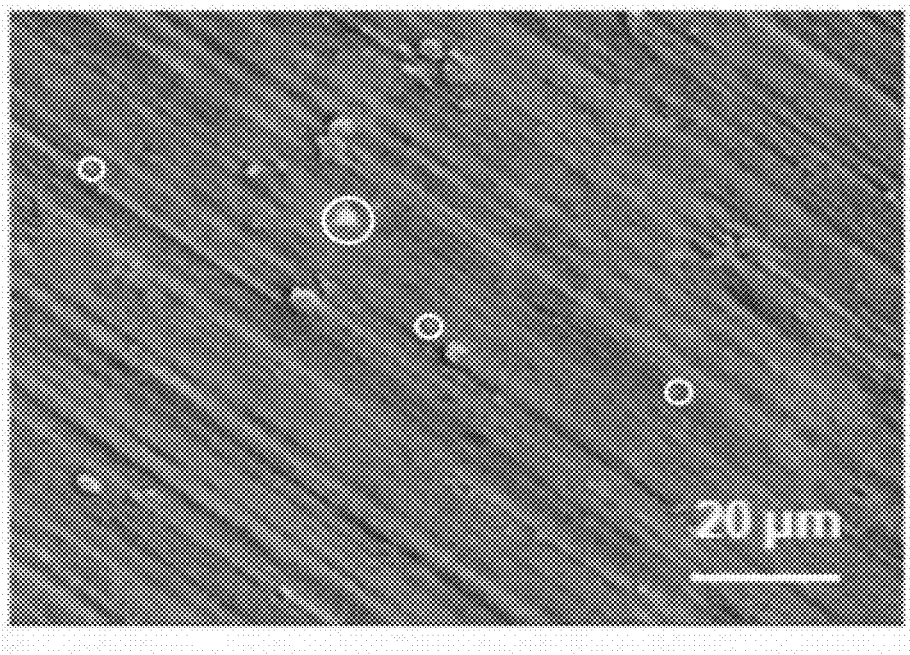
FIG. 8a-d show high resolution SEM images of titanium surfaces comprising $TiO_2$ particles of 8 nm (FIG. 8), 22 nm (FIG. 8b), commercial $TiO_2$ particles (FIG. 2c) and a reference surface without particles (FIG. 8d) after 12 hour of immersion in simulated body fluid.
Figure 8B:
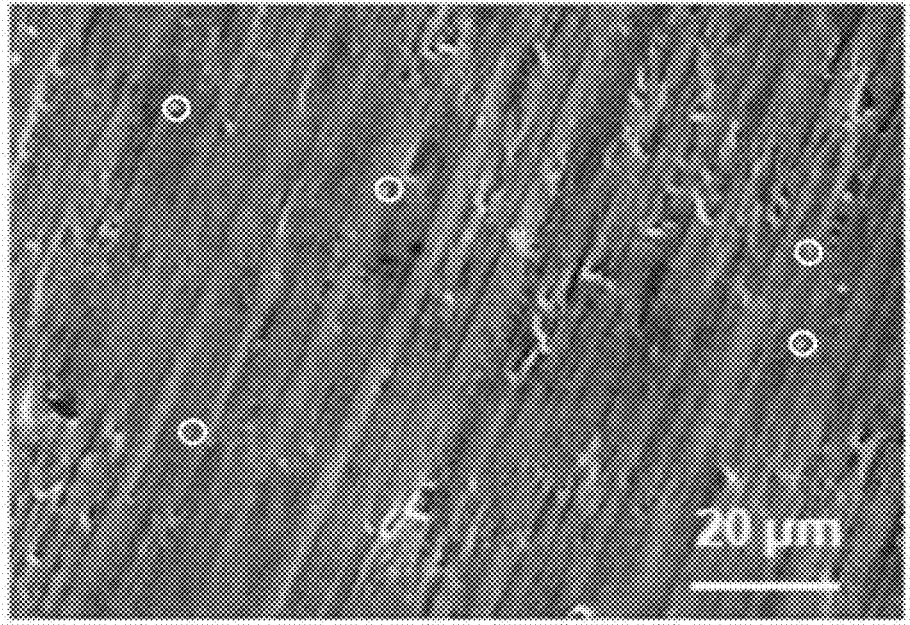
Figure 8C:
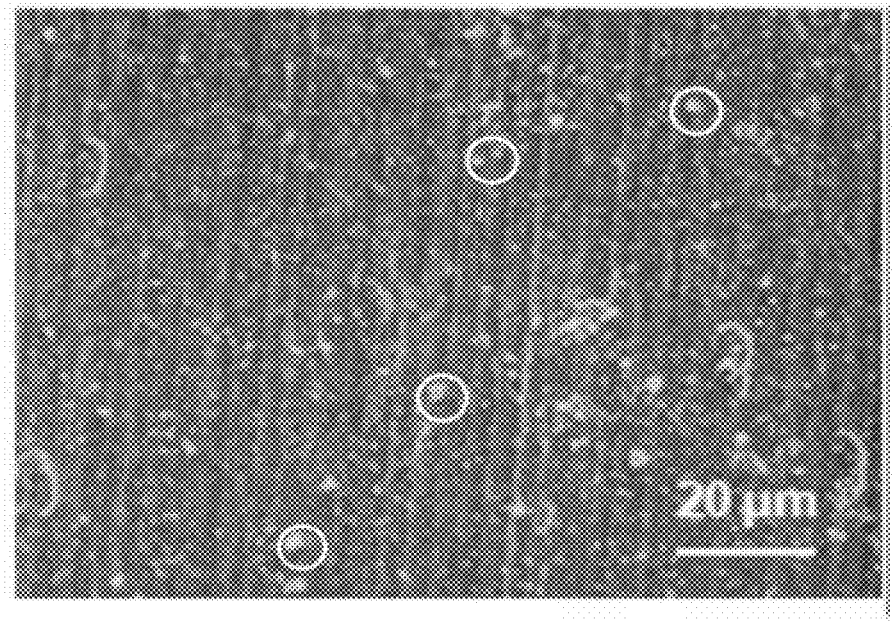
Figure 8D:
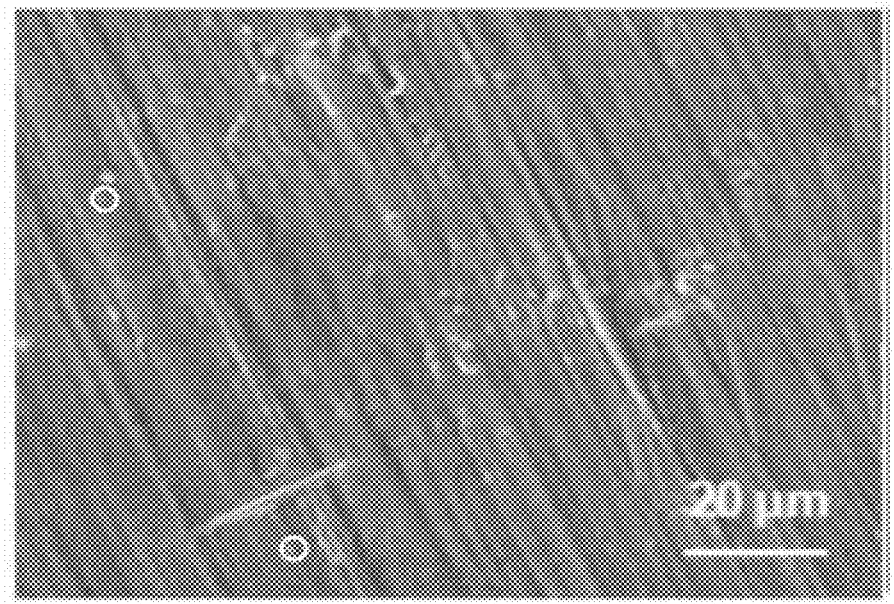
Figure 8E:
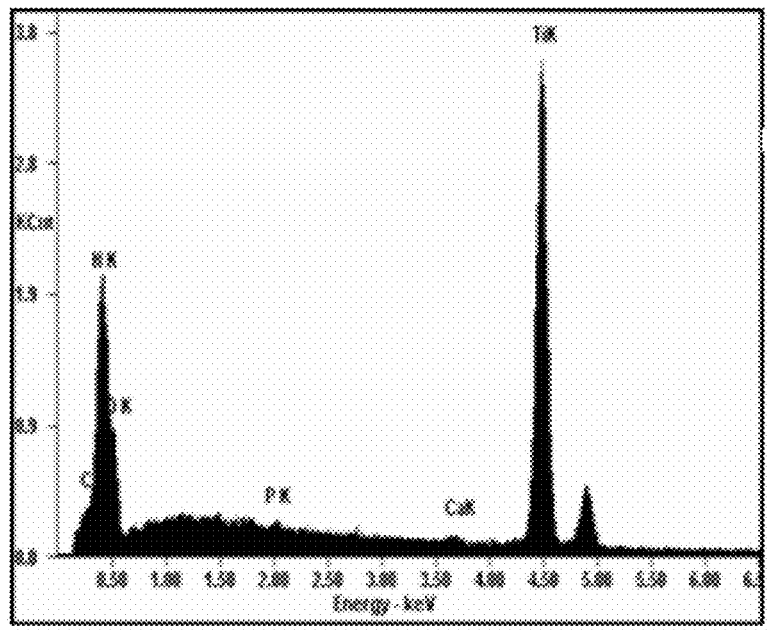
FIG. 8e-h show the EDX spectra and recorded atomic concentration of selected elements of the surfaces of FIG. 8a-d.
Figure 8F:
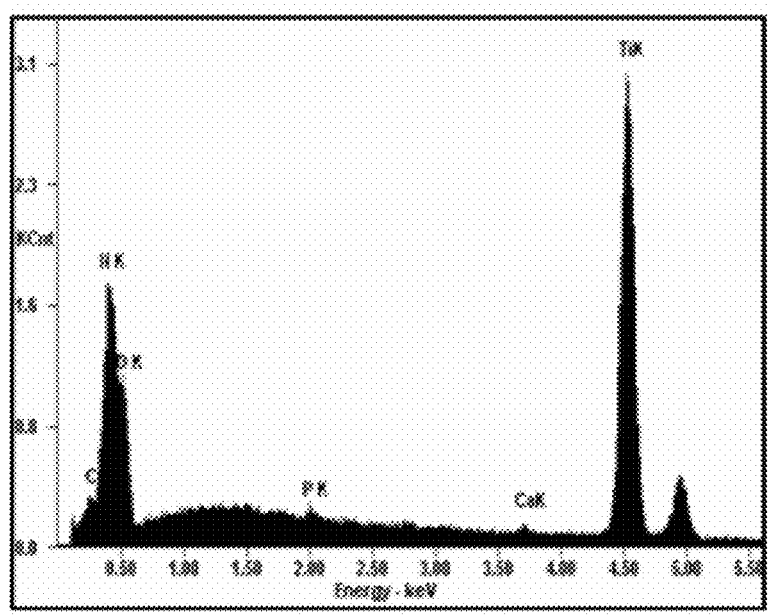
Figure 8G:
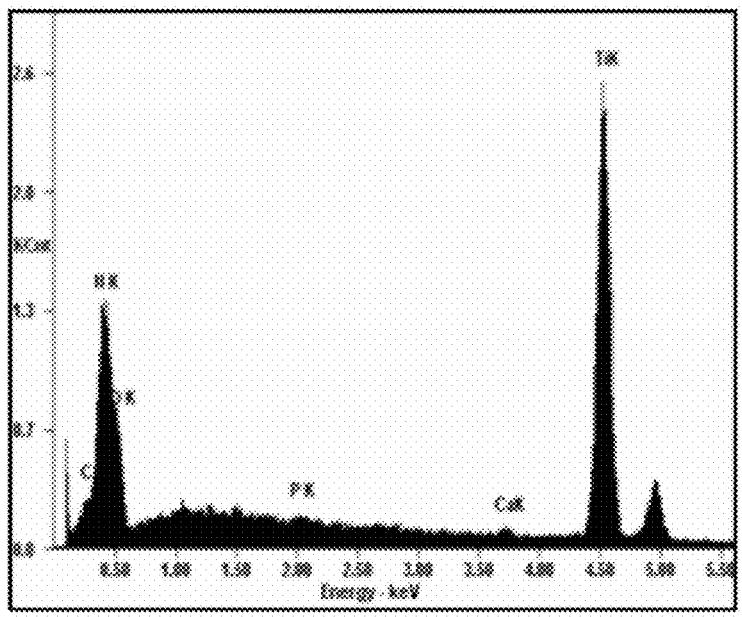
Figure 8H:
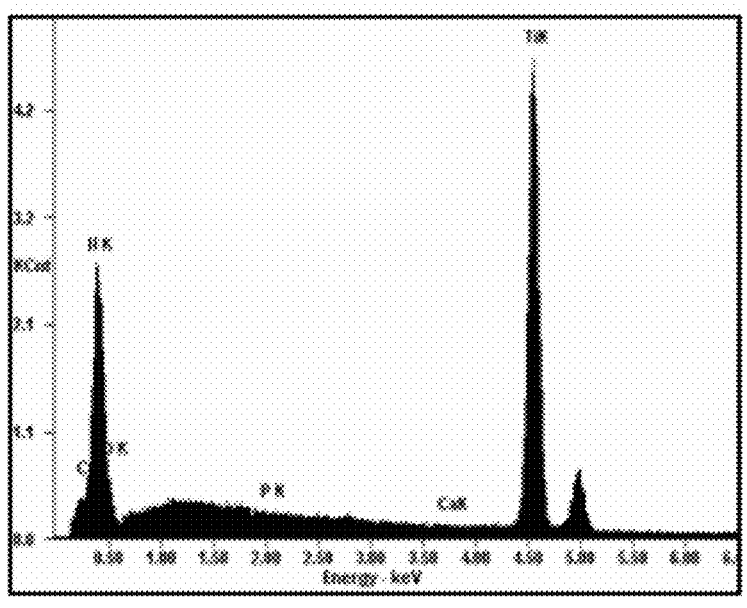

The results are shown in FIG. 7 and it is interesting to note that the early nucleation of apatite is significantly higher for surfaces comprising $TiO_2$ nanoparticles compared to the reference (TS) and the TS+AT1 surface. After 72 h immersion in SBF, the difference between the particle-containing surface and the reference has diminished and instead the TS+AT1 surface shows the highest apatite coverage. This trend is maintained after 1 week, FIG. 7. The morphology of the different surfaces was investigated by SEM and clear differences where obtained, FIGS. 8a-d show high resolution SEM images of the titanium surfaces TS+8 nm (FIG. 8a), TS+22 nm (FIG. 8b), TS+P25 (FIG. 8c), and the reference surface TS (FIG. 8d). Apatite crystal nucleation sites are seen and have been marked with circles. Furthermore, EDX analysis (measuring the energy released from electrons originating from electron shell K) confirms that higher amounts of calcium (Ca) and phosphorous (P) are present on the test surfaces (FIG. 8e-g) compared to the reference surface (TS, FIG. 8h). EDX analysis was performed only on a single point for each surface.

The influence of surface roughness on apatite formation has been previously investigated and with surface roughness corresponding to an $R_a$ value between 0.2 to 0.6 µm a continuous and adherent apatite layer has been shown to form on various materials. It is difficult to compare absolute values of roughness parameters due to differences in measuring techniques and analysis. However, relative values can be used and the results after 1 week of immersion support the previous findings that rougher surfaces favour formation of thick and adherent apatite layers compared to smoother surfaces, Table 2.

Fractured apatite layers with different characteristics were observed for all surfaces except for the TS+P25 surface.

Figures 9A, 9B, 9C:
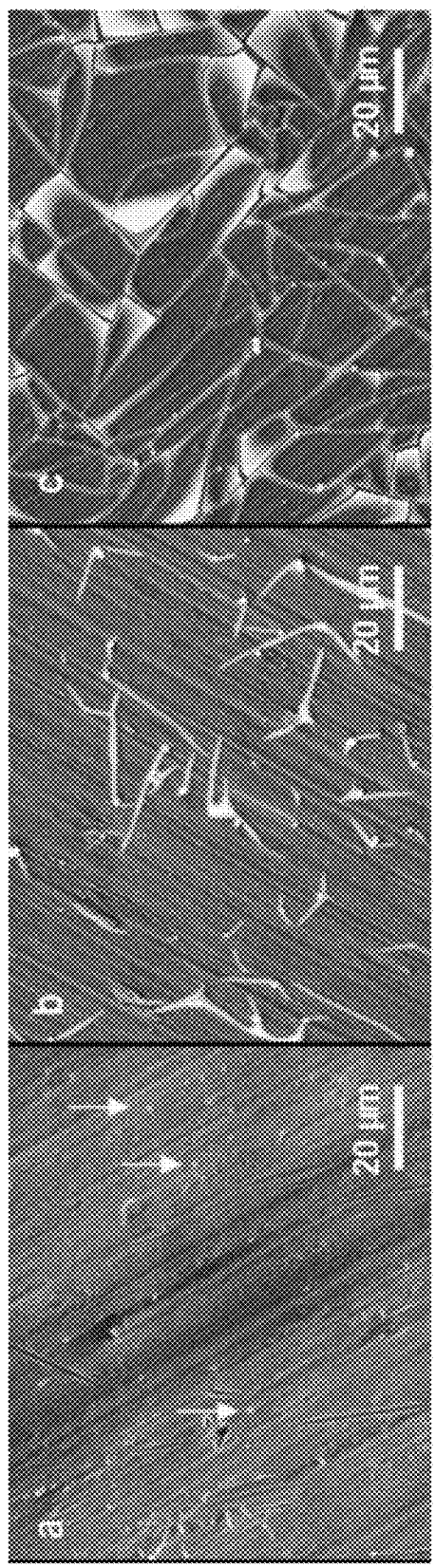
FIG. 9a-c are SEM images showing a titanium surface comprising 22 nm $TiO_2$ particles after 12 h (FIG. 9a), 72 h (FIG. 9b) and 1 week (FIG. 9c) of immersion in simulated body fluid.

The apatite layer formed on the TS+8 nm and TS+22 nm surfaces exhibited another type of fractures similar to those on apatite layers formed on titanium, first incubated in a fibronectin solution and thereafter in Hanks Buffer Saline Solution (HBSS) for one week (A. P. Do Serro, A. C. Fernandes and V. S. B. de Jesus, *J. Biomed. Mater. Res.*, 2000, 49, 345-352). The cracks or fractures have been suggested to be caused by drying shrinkage, and have been observed to be larger and deeper with increasing immersion time. An alternative explanation is related to the 3D growth mechanism for thick apatite layers, where nucleus on the surface grows and eventually forms a fully covering film. When the different nuclei start to interact, stresses are imposed and the apatite layer cracks. This mechanism seems to be valid for the TS+AT1 surface with no precipitates after 12 h but a fully covering film after 72 h. The mechanism of nucleation seems to be different for the surfaces with nanoparticles. The fast precipitation of hydroxyapatite at certain sites on the surface is followed by 2D growth, where the layer has weak interaction with the underlying substrate. The formation of a 2D layer seems to prevent the formation of bigger agglomerates commonly observed and as a consequence the layer remains thin. The early nucleation observed on surfaces covered with nanoparticles is illustrated for the TS+22 nm surface in FIG. 9. After 12 h, distinct precipitates are observed (marked with arrows in FIG. 9a) but the surface is not fully covered by precipitates. The Ca/P ratio of the precipitates at this stage is close to 1.7 (average of many test points) and no Ca and P signals were obtained in between the precipitates. This indicates formation of hydroxyapatite ($Ca_5(PO_4)_3(OH)$), which is the thermodynamically most stable phase. Hydroxyapatite is the main mineral in bone and is crucial to obtain high mechanical strength. After 72 h of immersion the surface is covered with a thin apatite layer and cracks start to form, FIG. 9b. It seems like the crack propagates from the initial precipitates due to stresses induced by the mismatch between the precipitates and the layer. After one week of immersion the apatite layer is fully developed but still thin, FIG. 9c.

In the present study, all surfaces (except TS+P25) had fractures irrespective of the surface roughness, Table 2. The apatite layers of the TS+8 nm and TS+22 nm surfaces seem to be detaching from the underlying surface. However, in this context it should be observed that in the in vivo situation, after implantation of a biocompatible component as described herein into living tissue, macromolecules such as proteins and proteoglykans, and cells would be attracted to the component surface within hours after implantation, and it is believed that their presence and/or activity would effectively prevent the formation of any 2-D or 3-D layer of apatite. Hence, the properties of an apatite layer formed after one week in vitro may be of little relevance to the in vivo implantation result. The Ca/P ratio of the formed apatite films was calculated from the EDX measurements and was found to range between 1.42-1.56 for all surfaces after 72 h and 1 week immersion. This could indicate formation of tricalciumphostphate ($Ca_3(PO_4)_2$) with Ca/P ratio=1.5.

The chemical composition of the formed apatite layers was analyzed by gracing angle-X-ray diffraction (GI-XRD). Although the EDX measurements show rather high apatite coverage for the TS, TS+8 nm, TS+22 nm and TS+P25 surfaces after 1 week, only weak and broad diffraction signals were obtained. This indicates that the layers formed are amorphous. Homogeneous growth from an SBF solution starts with formation of an amorphous phase with subsequent formation of small apatite crystals (Z. Z. Zyman, D. V. Rokhmistrov and V. I. Glushko, *J. Mater. Sci., Mater. Med.*, 2010, 21, 123-130).

For the TS+AT1 surface, where thicker apatite layers were obtained, clear diffraction peaks for hydroxy apatite are observed after 72 h and 1 week of immersion in SBF.

The long term results indicate that on a rougher surface the development of thick apatite layers is facilitated. However, the smoother surfaces containing nanoparticles show faster nucleation and formation of thin 2D layers of amorphous apatite. The correlation between the ability of a surface to induce nucleation of hydroxyapatite and in-vivo response has been investigated in T. Kokubo and H. Takadama, *Biomaterials*, 2006, 27, 2907-2915.

Thus, immersion in SBF solution can be a measure of the bioactivity of different surfaces. In the present study two types of nucleation and growth behaviours were observed. For the rougher surfaces the nucleation is initially delayed but once it starts, thick layers are formed. These layers have cracks induced by stresses in the film. For the smoother surfaces with small anatase nanoparticles, the initial precipitation is fast but only few small nuclei of hydroxyapatite is formed leaving the rest of the surface uncovered.

For surface films formed from small well dispersed nanoparticles, a porous layer is created on the surface. This results in both a larger donor density as determined from the impedance measurements and a larger active area compared with the turned surface and the surface containing agglomerates of P25. Moreover, the physical surface roughness seems to have an important role in the apatite formation since for the reference surface (TS), with rather high conductivity, apatite formation is limited. For the early nucleation the nanoparticle covered surfaces seems to be preferred.

EXAMPLE 3

Preparation and Characterization of Nanoparticle-coated Surfaces 3.1 Sample Preparation $TiO_2$ nanoparticles were synthesized by controlled hydrolysis of $TiCl_4$ as described above. By controlling reaction temperature, dialysis time/temperature and storage time and/or temperature, $TiO_2$ nanoparticles having a particle size of ~20 nm were obtained. The particles consisted predominantly of anatase with low traces of brookite. The particles were spincoated onto turned, degreased titanium discs according to the following schemes: For sample group A1 only one spincoating step was performed, while sample group A5 was subjected to spincoating five times. After spincoating, the samples were rinsed in water and left to dry at 50° C. for 5 minutes before being packaged and β-sterilized at 21kGy.

3.2 Sample Characterization

The two sample surfaces A1 and A5 were characterized using the following techniques:
- scanning electron microscopy (SEM) (XL30, FEI Company, 5651 GG Eindhoven, the Netherlands)
- field emission gun scanning electron microscopy (FEG-SEM) (Leo Ultra 55 FEG SEM)
- energy-dispersive X-ray spectroscopy (EDX or EDS) (XL30, FEI Company, 5651 GG Eindhoven, the Netherlands)
- X-ray photoelectron spectroscopy (XPS) (Quantum 2000 ESCA Scanning Microscope, Physical Electronics, Chanhassen, Minn. USA and CasaXPS software)
- X-ray diffraction (XRD) (Siemens D5000 powder diffractometer using CuKα radiation; λ=1.54056 Å)
- atomic force microscopy (AFM) (Nanoscope® Multimode IIIa, Digital Instruments)
- Contact angle measurements (EQ-Q-2857, SY-0302).

3.2.1 Scanning Electron Microscopy

Figure 10A:
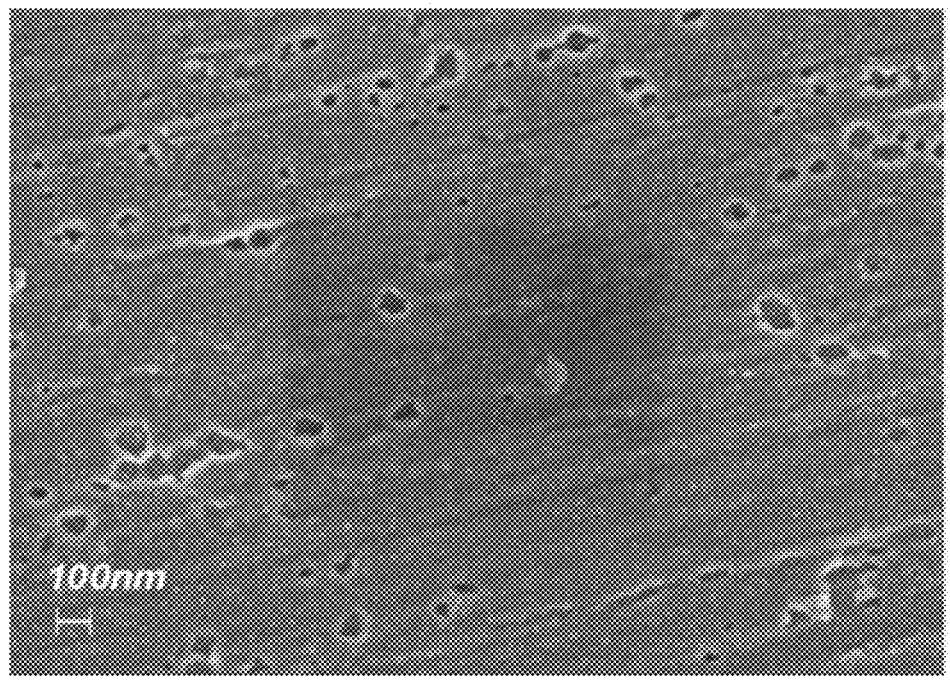
FIG. 10a-b are SEM images showing titanium surfaces covered with nanoparticles according to embodiments of the invention.
Figure 10B:
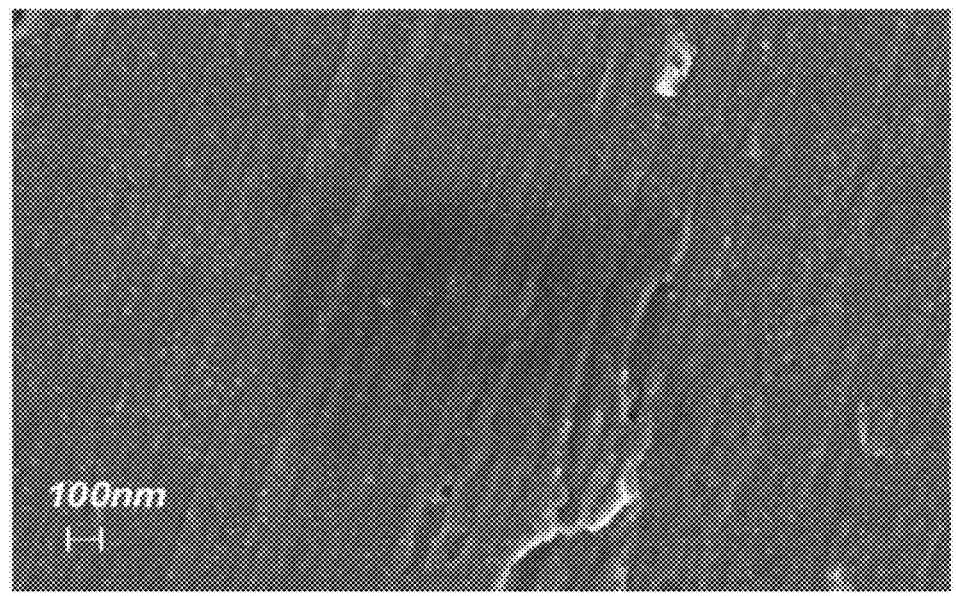

The morphology of the three different sample surfaces were investigated using SEM and FEG-SEM. FEG-SEM was primarily used to identify the nanostructured surfaces, A1 and A5, since discrete nanoparticles are impossible to detect using ordinary environmental SEM. In order to obtain images at higher magnifications, an inLense detector was used in combination with decreased potential and a resulting shorter working distance. An image of the A1 sample surface is shown in FIG. 10a and an image of the sample surface A5 is shown in FIG. 10b, both at magnification 100,000×. The thickness of the nanoparticle coating layer can not be seen in the images but the discrete nanoparticles are visible as small white dots on the surface.

In the SEM images shown in FIG. 10a-b the A1 and A5 surfaces look similar. However, there are differences in surface roughness. The surface roughness was determined using AFM, and will be further discussed below.

3.2.2 Energy-dispersive X-ray Spectroscopy (EDX)

Qualitative and quantitative elemental analysis of the overall element composition of the two samples A1 and A5 bulk material was determined using EDX. EDX collects information from a depth of approximately 1-2 μm, which means that only limited information about the outermost layer can be detected with this method. The analyses were performed at three different positions of each sample (two positions at different edges and one position in the middle of the sample) and at three different acceleration voltages (5, 15 and 30 kV) in order to study if the chemical composition varies with position and/or penetration depth.

From the elemental quantification it was observed that samples A1 and A5 have a similar composition. Since the values from the EDX analysis are relative, the ratio between oxygen/titanium, nitrogen/titanium and carbon/titanium were calculated respectively for the different samples and acceleration potentials, see Table 3. It can be seen that samples A1 and A5 have a similar elemental composition. Further, it can also be concluded that the ratios between oxygen, nitrogen or carbon, respectively, versus titanium decrease as a function of acceleration voltage (i.e., analysis depth) for both sample groups.

TABLE 3

Quantitative elemental ratio (at %) between carbon (C), nitrogen (N), oxygen (O), respectively. and titanium (Ti) as a function of acceleration voltage (15 and 30 kV respectively) as determined by EDX. (Mean values of 9 spots/sample group).

| Sample | C/Ti | N/Ti | O/Ti |
|--------|------|------|------|
| A1, 15 kV | 0.046 | 0.072 | 0.033 |
| A1, 30 kV | 0.035 | 0.041 | 0.023 |
| A5, 15 kV | 0.051 | 0.074 | 0.041 |
| A5, 30 kV | 0.035 | 0.051 | 0.033 |

3.3.3 X-ray Photoelectron Spectroscopy (XPS)

The chemical composition of the nanoparticle-coated surfaces was determined using X-ray photoelectron spectroscopy (XPS), data presented in Table 4. The two sample surfaces A1 and A5 have a similar chemical composition and show mainly the presence of titanium, oxygen and carbon. High amounts of carbon were detected for both samples due to the manual sample preparation procedure. No trace of chloride from the nanoparticle synthesis was identified for either sample surface.

Extended analysis of the detected elements using Casa XPS software was also performed. The binding energies of Ti2p1/2 and Ti2p 3/2 were observed at 465 and 459 eV for all samples. The doublet is attributed to Ti(IV) and shows that $TiO_2$ is the main constituent on the sample surfaces. For both surfaces A1 and A5 also the Ti metal doublet at 454.6 eV and 461.4 eV respectively were identified. The Ti metal peak originates from the underlying titanium substrate and can be identified on surface A1 and A5 since the $TiO_2$ nanoparticle coatings are thin.

Both sample surfaces showed the clear O1s peak at 531 eV originating from the Ti—O bonds. In addition, a shoulder at higher binding energies was observed. Deconvolution of the O1s spectra gave a peak at 533 eV which originates from oxygen bound to carbon. As for the O1s spectra the C1s spectra showed a dominant species with a shoulder at higher binding energies. The dominant peak at 285.5 eV has been attributed to the presence of hydrocarbons (C—C and C—H) and is often seen on oxide layers under atmospheric conditions. The shoulder at higher binding energies (289 eV) has been attributed to C—O and C═O species respectively.

TABLE 4

Quantitative surface composition (at %) of A1 and A5 samples as determined by XPS (three specimens of each group were analyzed).

| Sample | Position | C1s | N1s | O1s | NaKL | Si2p | Ti2p |
|---|---|---|---|---|---|---|---|
| A1-1 | Middle | 24.4 | 1.2 | 51.4 | — | — | 23.0 |
| A1-1 | Edge 1 | 31.6 | 0.4 | 48.7 | — | — | 19.3 |
| A1-1 | Edge 2 | 26.1 | 0.8 | 50.4 | — | — | 22.6 |
| A1-2 | Middle | 26.6 | 0.6 | 50.7 | — | — | 22.1 |
| A1-2 | Edge 1 | 30.6 | 1.1 | 48.6 | — | — | 19.7 |
| A1-2 | Edge 2 | 28.4 | 1.2 | 49.2 | — | — | 21.2 |
| A1-3 | Middle | 39.1 | 0.9 | 41.8 | — | — | 18.2 |
| A1-3 | Edge 1 | 33.6 | 0.6 | 48.0 | — | — | 17.8 |
| A1-3 | Edge 2 | 25.8 | 1.0 | 50.4 | — | — | 22.8 |
| A5-1 | Middle | 38.5 | 0.8 | 41.2 | — | 0.3 | 19.1 |
| A5-1 | Edge 1 | 32.6 | 0.6 | 48.1 | — | — | 18.7 |
| A5-1 | Edge 2 | 38.2 | 0.9 | 42.4 | — | — | 18.6 |
| A5-2 | Middle | 22.1 | 0.8 | 53.3 | — | — | 23.8 |
| A5-2 | Edge 1 | 27.1 | 0.7 | 51.4 | — | — | 20.9 |
| A5-2 | Edge 2 | 22.0 | 0.9 | 52.9 | — | 0.4 | 23.8 |
| A5-3 | Middle | 22.6 | 0.3 | 52.8 | — | 0.3 | 24.0 |
| A5-3 | Edge 1 | 32.3 | 0.2 | 49.3 | — | — | 18.2 |
| A5-3 | Edge 2 | 22.1 | 1.0 | 53.5 | — | — | 23.5 |

3.3.4 X-ray Diffraction (XRD)

X-ray diffraction measurements were performed on surfaces A1 and A5 respectively. All the seven titanium metal signals were represented for both sample surfaces. The metal signals were not randomly oriented as for a single crystal surface which is probably due to cold work of the bulk material. No signals from titanium dioxide (rutile) was present on the surface which is probably due to the oxide layer being thin. The lack of oxide peaks can also indicate that the oxide is x-ray amorphous, i.e., the grain size is beyond Bragg's limits so that no clear reflection pattern can be obtained.

3.3.5 Atomic Force Microscopy (AFM)

Figure 11A:
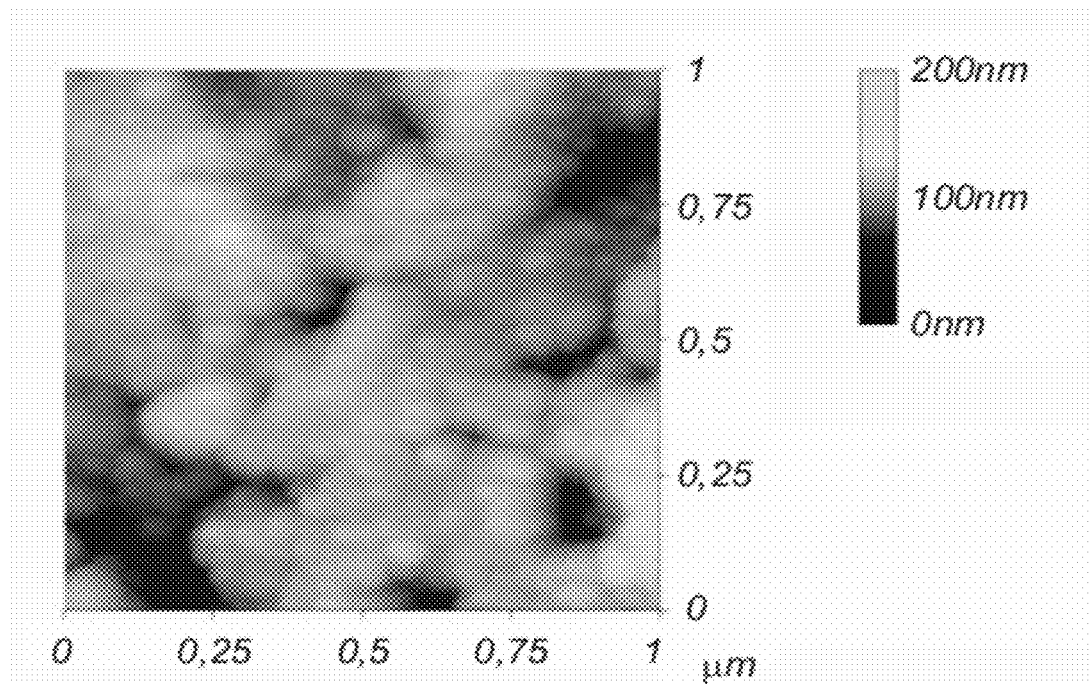
FIG. 11a-b are AFM images of surfaces coated with nanoparticles according to embodiments of the invention.
Figure 11B:
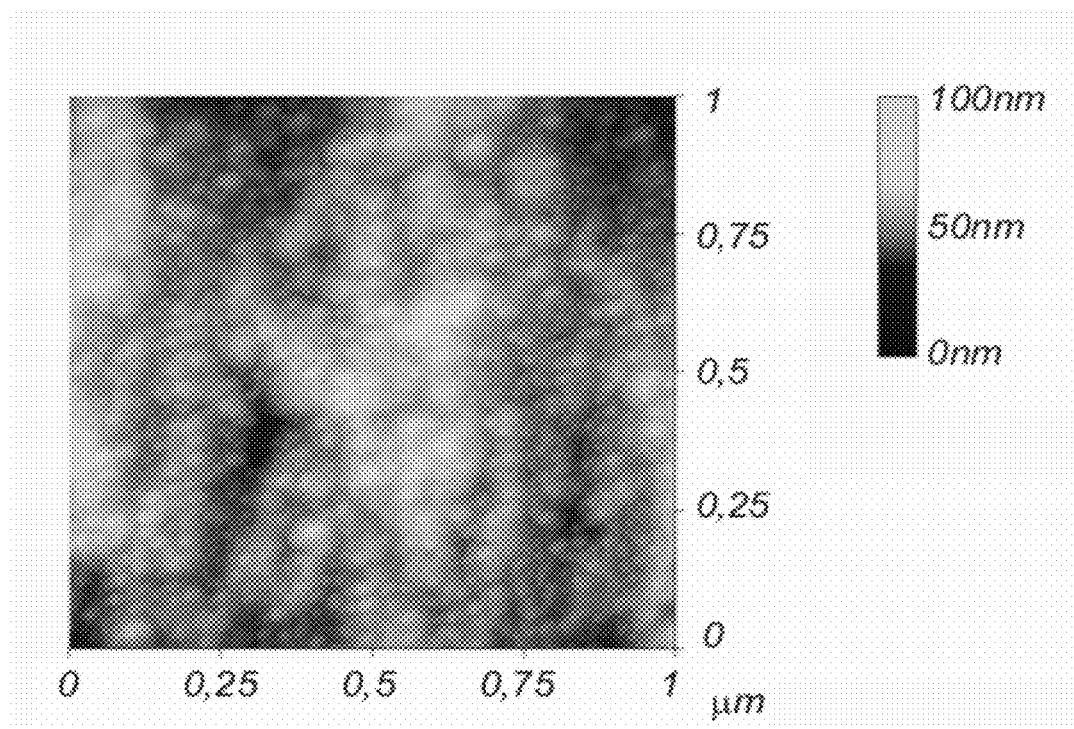

In order to further investigate the surface roughness also AFM images were recorded. FIG. 11a shows the A1 surface, and FIG. 11b shows the A5 surface. The 3D-surface roughness parameters were calculated using the MeX® software and values for three different parameters are listed in Table 5.

From the AFM images it can be observed that the surfaces A1 and A5 have an additional surface structure on top of the turned surface.

From the SEM images of sample A1 (FIG. 10a) and A5 (FIG. 10b) These two surfaces look quite similar with the underlying substrate covered to the same extent. However, when studying the AFM images, FIG. 12a-b, it is clear that this is not the case. For sample A5 (FIG. 11b) the underlying substrate is fully covered with several layers of nanoparticles inducing a thick, smoothening oxide film. Sample A1 (FIG. 11a) also has a covering coating of nanoparticles although the structure is not as smooth as that of A5. This is also verified by the surface roughness parameters in Table 5 where it can be seen that the $S_a$ value of A1 is somewhat higher compared to that of A5. The root mean square of the slope ($S_{dq}$) has been shown to correlate with the interface shear strength and is thus an important parameter to investigate for dental implant applications. From a biomechanical point of view a large $S_{dq}$ value is desired, giving surface A1 a small advantage as compared to A5. The trend in $S_{dr}$ (developed interfacial area) values follows the same trend as the $S_a$ and $S_{dq}$ values with the smallest value obtained for the surface with the thickest nanoparticle layer i.e. A5.

TABLE 5

Surface roughness parameters as determined by AFM.
Data from 5 × 5 μm scan
size and a Gaussian filter of 20% of the horizontal width.

| Sample | $S_a$ (nm) | $S_{dq}$ | $S_{dr}$ (%) |
|---|---|---|---|
| A1 | 10.91 (2.11) | 0.42 (0.08) | 8.45 (3.01) |
| A5 | 6.88 (1.78) | 0.31 (0.05) | 5.06 (1.18) |

3.3.6 Contact Angle

The hydrophilicity of the surfaces A1 and A5 was determined using contact angle measurements. Both samples surfaces were hydrophilic according to the usual definition i.e., contact angles <90°, see Table 6.

TABLE 6

Contact angles of samples A1 and A5.

| Sample | Contact angle (°) |
|---|---|
| A1 | 76.6 (3.1) |
| A5 | 84.6 (6.6) |

3.3 Discussion

The A1 and A5 samples were prepared from the same type of substrate, i.e., turned titanium (Grade 4) discs. In both cases a spincoated layer of nanoparticles is covering the underlying substrate. The nanostructures were too small to be identified using an ordinary environmental SEM and therefore the samples were analyzed by a high resolution FEG-SEM. In these images the surfaces A1 and A5 look quite similar with discrete nanoparticles or groups of nanoparticles deposited on top of the underlying metal structure. However, when comparing the SEM images with the AFM images, it is obvious that the underlying surface structure is completely covered with a film of nanoparticles, forming a continuous coating. Sample group A1 had only been spin coated once, while for sample group A5 the spincoating procedure was repeated five times resulting in a much thicker coating. This was also verified by the surface roughness measurements which show a lower $S_a$ value for the surface A5 as compared to A1.

The contact angle measurements showed that both samples were hydrophilic. The XPS analysis showed that the samples were clean and the surface mainly cinstituted by titanium, oxygen and carbon, and also indicated that $TiO_2$ is the main constituent present on the sample surfaces. In addition, for both samples A1 and A5 the Ti metal signal can be observed, indicating that the nanoparticle coatings are thin, although the A5 coating is thicker than the A1 coating.

Although the XPS analysis showed that both sample surfaces were covered by $TiO_2$, the XRD analysis did not show any reflexions from the oxide. The oxide cannot be verified by XRD since the layers are too thin.

EXAMPLE 4

Adherence of the Nanoparticle Coating 4.1 Sample Preparation

A solution of $TiO_2$ nanoparticles having a particle size of 19.5 nm was prepared in accordance with Abbas et al, Nanoparticles Colloids and Surfaces A: Physiochem. Eng. Aspects 384 (2011) 254-261. The nanoparticle solution was spincoated onto commercially pure and cleaned titanium fixtures (turned, no blasting or acid etching) as follows: The fixture was mounted on a sample holder and dipped into nanoparticle solution during rotation of 1400 rpm. After dipping into the nanoparticles solution the fixture was dipped in rinsing water. The fixture was then rotated at 4500 rpm for about 30 s for removal of remaining water. The fixture was dried in an oven at 50° C. for a few minutes.

Figure 12:
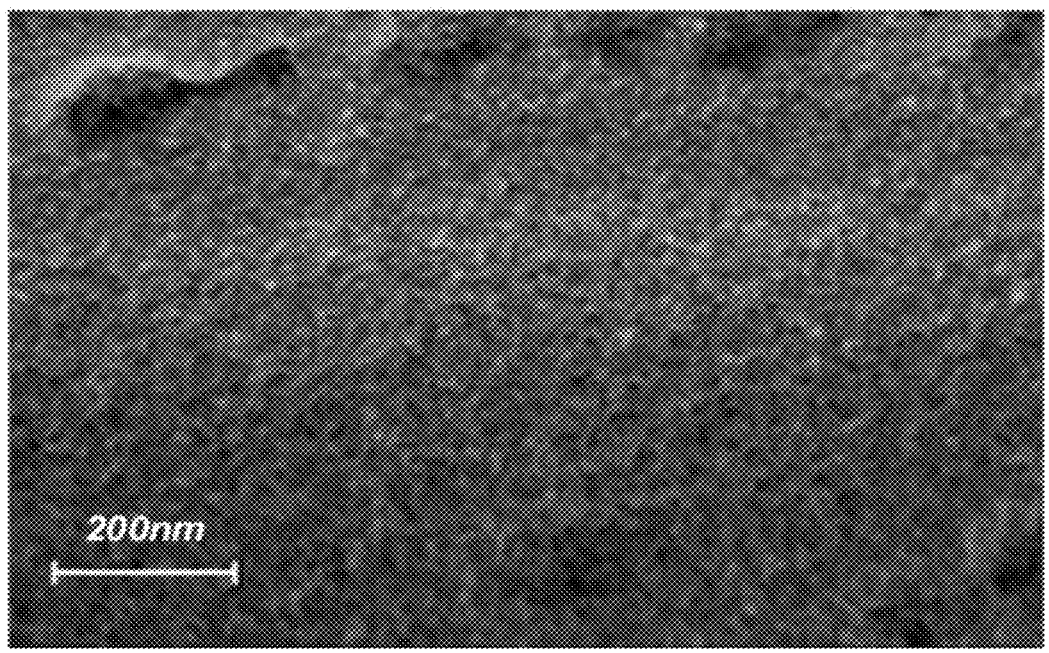
FIG. 12 is an FEG-SEM image at 250,000× magnification of a titanium fixture coated with nanoparticles according to embodiments of the invention.

The fixtures were evaluated with FEG-SEM at magnification 250,000×, shown in FIG. 12. The analysis revealed that the surface exhibited nanoparticles.

4.2 Evaluation after Installation in Bone

Figure 13:
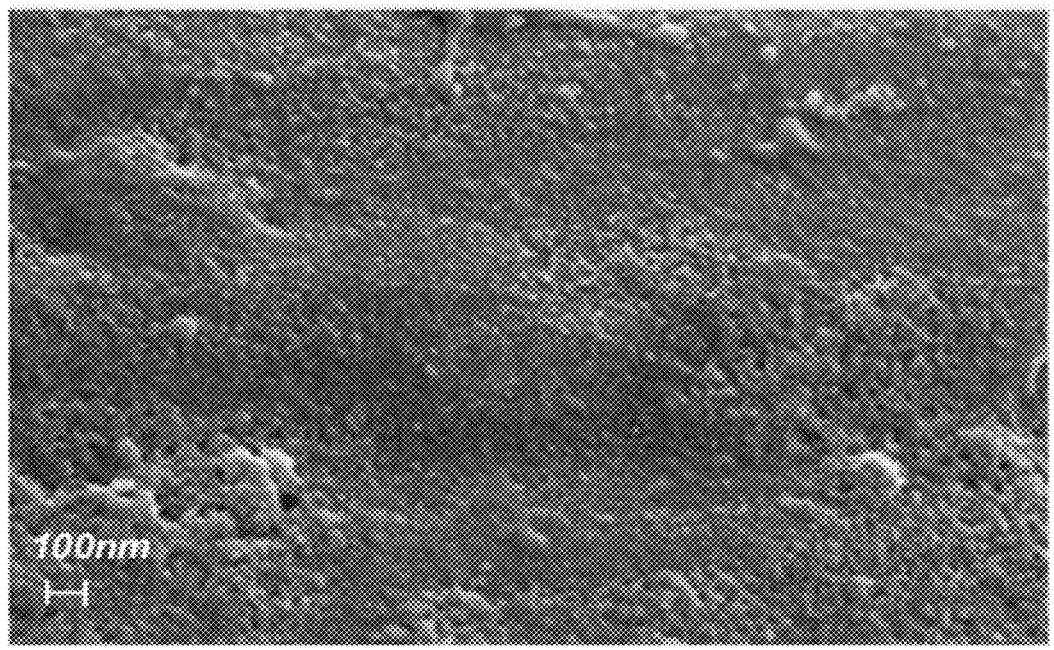
FIG. 13 is an FEG-SEM image at 100,000× magnification of a titanium fixture coated with nanoparticles according to embodiments of the invention after installation into and removal from calf bone.

Tests were performed to investigate if the nanoparticle coating remains pn the surface after fixture installation in dead calf bone, removal from the bone and the following washing procedure. The results showed that in the nanoparticle coating seems to be unaffected by fixture installation in calf bone and also stands intact with following washing procedure. FIG. 13 is a FEG-SEM image at 100,000× magnification showing a nanoparticle coated titanium fixture after being removed from the calf bone and cleaned. Some bone residuals remained on the surface. The nanoparticles were still adhered also on top of the threads.

EXAMPLE 5

Evaluation of Cell Response In Vitro

The effect of sample surfaces prepared according to Example 3.1 above was evaluated using laboratory based assays for cell proliferation and osteogenic differentiation markers using a human derived mesenchymal stem cell model.

5.1 Samples

In addition to the samples A1 and A5 described above, machined commercially pure titanium discs ("Ti") were used as control.

5.2 Cell Culture

Human palatal mesenchymal cells (HEPM 1486; ATCC) were cultured in Eagles Minimal Essential Media (EMEM) with Earl's Salts with 10% fetal bovine serum (FBS) with Pen/Strep antibiotics [25 mg/ml], and ascorbate [50 mg/mL], NaPyruvate [1 mM], non essential amino acids [0.1 mM], L-glutamine [2 mM] cultured with 5% $CO_2$. Cell culturing entailed isolating HEPM cells via typsin, counting (with a hemocytometer), pelleting and suspension at 50,000 cells/10 μl. 10 μl of cell suspension (Micromass approach) was plated on each test and control surface, the culture allowed to adhere for 1 hour before gentle flooding with 1 ml of EMEM+10% FBS (Stanford, Jacobson et al, 1995, Journal of Biological Chemistry 270(16):9420-9428).

For the assays, 3 disks/group/time point were used. The assays were performed though day 14 with assay endpoints on day 0, 1, 4, 8 and 14. The zero time point was an aliquot of the cell suspension made prior to plating. Change of media was done every four days. 100 μl of media were collected from each well of a twenty four well dish in which the discs are incubated.

Collected media were stored for proteomic assay for bone-related protein expression. Media collection for the proteomic measurement from the media was made at days 0, 1, 2, 4, 6, 8, 12.

5.3 Cell Proliferation and Cell Activity 5.3.1 Cell Proliferation Assay

Cell proliferation was measure over a 14 day period using a standard MTT assay. Vybrant MTT Cell Proliferation Assay (Molecular Probes Kit V-13154) is a microplate absorbance assay, which uses the conversion of water soluble MTT (3-(4,5-dimethylthiazol-2-yl)-2,5-diphenyltetrazolium bromide) into an insoluble formazan. The formazan is then solubilized and read in a microtiter plate reader at 570 nm.

Microdots (50,000 cells/10 μl media) of HEPM cells were placed onto discs in a 24-well plate. After 1 hour (to allow cell attachment) the discs were flooded with 1 ml EMEM supplemented with ascorbate [50 mg/ml]. The media also contained 10% FBS and Pen/strep. After 24 hours the Invitrogen Vybrant MTT Cell Proliferation Assay was followed to collect samples for day 1. The samples were incubated over night at 37° C. in SDS-HCl solution, then mixed and read at an absorbance of 570 nm. This procedure was repeated for samples at day 2, day 4, day 6, day 8 and day 14.

Cell proliferation was compared to a standard curve. The following was observed:

Day 1: All surfaces showed that cells were attached and viable on the A1 and A5 surfaces compared to the Ti at day 1. An increased number of cells was noted on the A1 surface compared to Ti.

Day 4: The A1 and A5 surfaces showed decreased number of cells compared to Ti.

Day 8: After 8 days both A1 and A5 surfaces showed a decreased number of cells compared to the Ti surface.

Day 14: The cells on the A1 and A5 surfaces recovered, showing similar number of cells to the Ti after 14 days.

5.3.2 Gene Expression Levels of Bone Related Gene Markers

Changes in osteoblast gene expression for alkaline phosphatase, cbfa1, osteocalcin and BMP-2 were analyzed using multiplex and real time PCR strategies at day 0, 1, 4, 8 and 14. Micromass cultures (50,000 cells/10 μl media) were plated in triplicate on plastic as a control as previously described (Schneider, Zaharias et al., 2004. Journal of Biomedical Materials research. 69A 3:462-468) After 1 h of attachment, wells were flooded with EMEM/10% FBS and 50 mg/ml ascorbate. At days 0, 1, 4, 8 and 14, total cell RNA was extracted with RNeasy Mini Kit (Qiagen), according to manufacturer instructions. Cells were then homogenized (QIAshredder column, Qiagen) and applied to the RNeasy column, rinsed and eluted. RNA concentration was calculated from the absorbance at 260 nm, and RNA purity determined from the ratio of 260 and 280 nm absorbance. Using the extracted RNA as a template, reverse transcription reactions were carried out with TaqMan Reverse Transcription Reagents (Applied Biosystems) and the RT reactions performed in a PTC-200 Peltier Thermal Cycler (MJ Research). After an initial 10 min at 25° C., the reaction mixture was incubated at 48° C. for 30 min, heated at 95° C. for 5 min, and subsequently chilled to 4° C. The TaqMan Ribosomal RNA Control Reagents Kit (Applied Biosystems) was used to detect 18s ribosomal RNA as an endogenous control.

Then, the alkaline phosphatase, cbfa1, osteocalcin, and BMP-2 target and the endogenous rRNA control were amplified by multiplex PCR with thermal cycling parameters of 50° C. for 2 min, 95° C. for 10 min, 40 cycles of 95° C. for 15 sec, and 60° C. for 1 min, using TaqMan Universal PCR Master Mix (Applied Biosystems). The real-time PCR reactions were performed in 96-well Optical Reaction Plates (Applied Biosystems) in an ABI Prism 7300 Real Time PCR Detection System. RNA Extraction and RT-PCR protocols for the osteogenic genes (only BMP-2 and cbfa1 illustrated here) were following the methods described by Perinpanayagam, H. (2002). Briefly, cultures were harvested, rinsed in PBS and total cell RNA extracted. Real-time PCR primers and probes for RUNX-2/Cbfa1 were designed with Primer Express software (Perkin Elmer) from the 294 bp of known rat sequence that correspond to exons 1 and 2 of the gene (Xiao et al. (1998) Journal of Biological Chemistry, 273(49): 32988-32994), generating an 80 by product that overlaid an exon junction. The DNA probe was modified with the 5'-reporter dye FAM (6-carboxyfluorescein) and the 3'-quencher dye TAMRA (6-carboxy-N,N,N',N'-tetramethylrhodamine). In each reaction tube, Cbfa1 levels were normalized to 18S rRNA by calculating $\Delta Ct$, where $\Delta Ct=$ (FAM)Ct−(VIC)Ct. A constant was subtracted to give $\Delta\Delta Ct$, where $\Delta\Delta Ct=\Delta Ct-k$ (k was adjusted to approximate the lowest $\Delta Ct$ value). The relative levels of cbfa1 were calculated as $2^{(-\Delta\Delta Ct)}$.

The following results were noted at the different time points:

Day 1: No differences in gene expressions of BMP-2, cbfa1, alkaline phosphatase or osteocalcin on the test surfaces compared to the Ti.

Day 4: Increased expressions of BMP-2 and cbfa1 on surface A1 and a small increased expression of alkaline phosphatase on A5, but a decreased expression of osteocalcin on all test surfaces.

Day 8: Increased BMP-2 response on all test surfaces showing significant higher value on the A1 surface compared to Ti. The cbfa1 expression showed higher level on the A5 surface and comparable level on the A1 to the Ti control surface. In general low levels of the alkaline phosphatase expression on all surfaces were observed.

Day 14: Significantly increased BMP-2 expression on the A1 surface. The Ti control and A1 presented similar levels of cbfa1 expression but the A5 surface showed an increased level compared to the control (Ti). Compared to the control no alkaline phosphatase or osteocalcin expression levels were elevated. Low levels of alkaline phosphatase.

Figure 14:
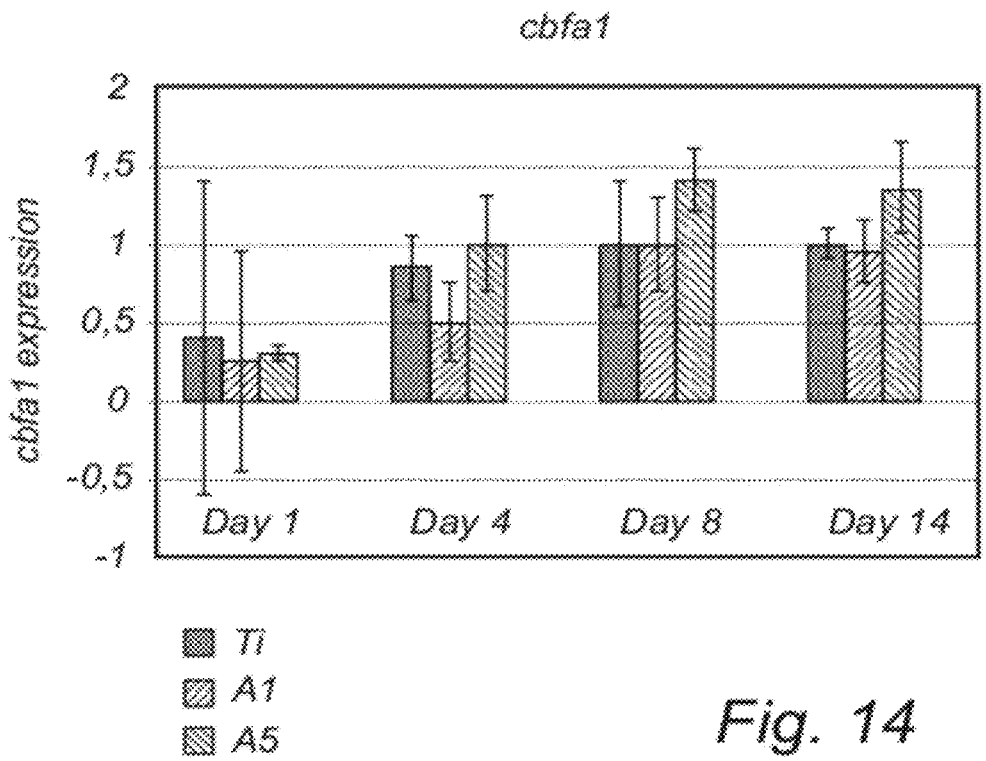
FIG. 14 is a graph showing the gene expression level of cbfa detected in osteoblasts grown on surfaces according to embodiments of the invention.
Figure 15:
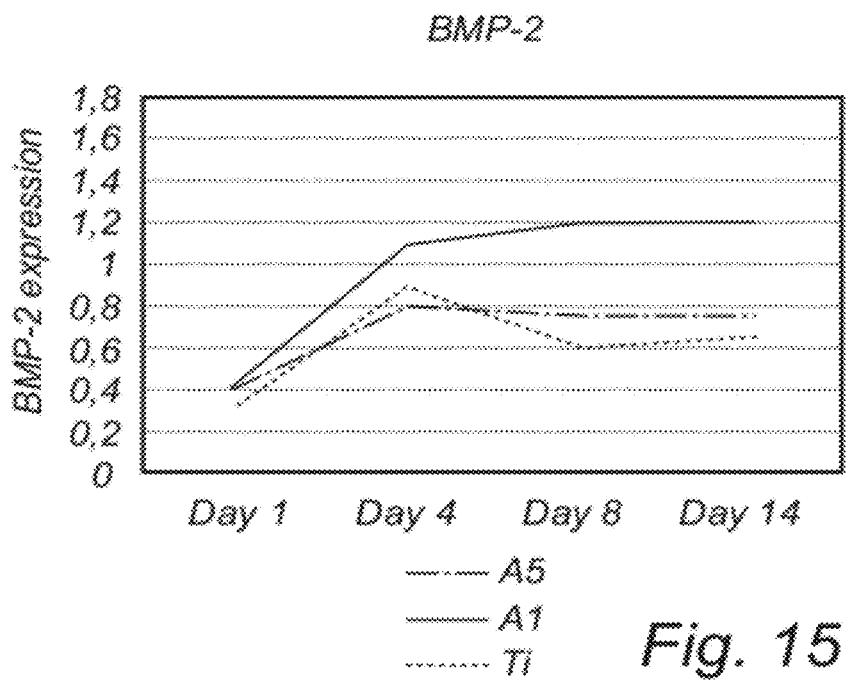
FIG. 15 is a graph showing the gene expression level of BMP-2 detected in osteoblasts grown of surfaces according to embodiments of the invention.

The cbfa expression is illustrated in FIG. 14, and BMP-2 expression is illustrated in FIG. 15.

5.3.3 Protein Level Measurements

A multiplex kit was selected that provided the most objective measures of osteogenic protein markers (osteocalcin, osteopontin and osteoprotegrin) expressed in vitro. Briefly, 50 µl cell culture supernatants were incubated with anti-human multi-protein marker beads at 4° C. for 18 hours with unbound material removed by filtration (Assay Millipore, Billerica, Mass., USA). 25 µl of anti-human multi-peptide biotin reporter was added, and reactions incubated at room temperature for 1.5 hours in the dark. 25 µl of streptavidin-phycoerythrin was added, and the plates incubated at room temperature for an additional 30 minutes. 25 µl of stop solution was added, and the plates read in a plate reader (Model 100 IS, Luminex, Austin, Tex., USA). Concentrations of cytokines IL-6 and TNF-α in each sample were extrapolated from standards (2.3-to-10,000 pg/ml) using Beadview software (Millipore, Billerica, Mass., USA).

Figure 16:
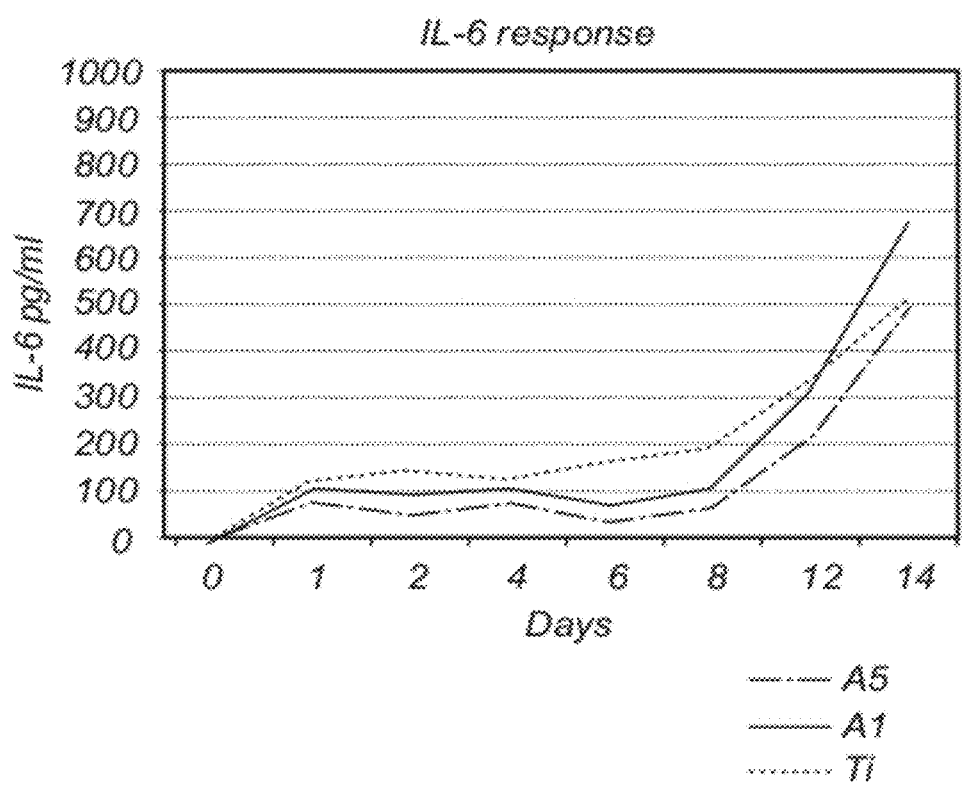
FIG. 16 is a graph showing the level of IL-6 secreted by osteoblasts grown on surfaces according to embodiments of the invention.

All surfaces followed an ordinary healing process showing no extra high protein levels on any of the surfaces. The proinflammatory cytokines TNF-α and IL-6 showed an increased levels of IL-6 after 8 days and after 14 days the highest values were noted on the A1 surface. The IL-6 response is illustrated in FIG. 16.

5.3.4 Summary and Conclusions

The test surfaces showed in general a proliferation comparable to the Ti control surface. In general the proliferation was more noted than the differentiation. This was shown by the low activity of the alkaline phosphatase expression peaking at day 4 but decreasing at later time points. The osteoinductive BMP-2 was only noted for the A1 surface from day 4 through day 14. The osteoblast differentiation marker cbfa1 was increased on A5 from day 4 through day 14.

The small increased IL-6 levels on the test surfaces might reflect the BMP-2 late response.

The nanoparticle coated surfaces A1 and A5 have a small effect on differentiation but the general trend is that these surfaces promote the proliferation of osteoblasts in this in vitro study.

The invention claimed is:

1. A biocompatible component having a surface intended for contact with living tissue, wherein the surface comprises particles of metal oxide, said particles having an average particle size of less than 25 nm, and wherein said particles form at least one layer, each layer having a thickness in the range of from 8 nm to about 1 µm; wherein the particles of metal oxide comprise particles of titanium dioxide and one or more particles selected from the group consisting of an oxide of zirconium, hafnium, vanadium, niobium, tantalum, cobalt and iridium and wherein the predominant form of said titanium dioxide is anatase and wherein the particles have a particle size distribution of up to 40%.

2. The biocompatible component according to claim 1, wherein the particle size distribution, taken as the ratio between the full width at half maximum (FWHM) divided by the mean particle size, is obtained by electrospray-scanning mobility particle sizer (ES-SMPS).

3. The biocompatible component according to claim 1, wherein said particles have a spherical shape.

4. The biocompatible component according to claim 1, wherein the metal oxide is at least partly crystalline.

5. The biocompatible component according to claim 1, wherein each layer of said at least one layer has a thickness in the range of from 50 nm to 500 nm.

6. The biocompatible component according to claim 1, wherein said at least one layer is a monolayer of said particles.

7. The biocompatible component according to claim 1, wherein said at least one layer is a continuous layer of said particles.

8. The biocompatible component according to claim 1, wherein said at least one layer completely covers said surface.

9. The biocompatible component according to claim 1, wherein said particles are homogeneously distributed throughout said at least one layer.

10. The biocompatible component according to claim 1, wherein said particles are non-sintered.

11. The biocompatible component according to claim 1, wherein at least some of said particles are sintered particles.

12. The biocompatible component according to claim 1, wherein said surface has an electrochemically relative active surface area ($A_{aa}$) of at least 1.5, compared to a corresponding biocompatible component which lacks said particles and has a surface covered by native metal oxide.

13. The biocompatible component according to claim 1, wherein said biocompatible component comprises a substrate having said surface, which substrate comprises a metallic material.

14. The biocompatible component according to claim 13, wherein said metallic material is selected from titanium, zirconium, hafnium, vanadium, niobium, tantalum, cobalt and iridium, and alloys thereof.

15. The biocompatible component according to claim 1, wherein a part of the substrate that is in contact with said particles comprises titanium oxide.

16. The biocompatible component according to claim 1, wherein said biocompatible component is intended for implantation into living tissue.

17. The biocompatible component according to claim 16 which is a dental implant, preferably a dental fixture.

18. The biocompatible component according to claim 16, which is an orthopedic implant.

19. The biocompatible component according to claim 1, wherein nucleation of hydroxyapatite crystals forms on the surface of said biocompatible component within 12 hours when immersed in simulated body fluid.

20. A method of producing a biocompatible component, comprising the steps of:
  a) providing a substrate having a surface intended for contact with living tissue;
  b) providing a dispersion of particles of metal oxide in a solvent, which particles have an average particle size of less than 25 nm; and
  c) applying said dispersion of particles onto the surface of said substrate;
  wherein said particles form at least one layer, each layer having a thickness in the range of from 8 nm to about 1 μm; wherein the particles of metal oxide comprise particles of titanium dioxide and one or more particles selected from the group consisting of an oxide of zirconium, hafnium, vanadium, niobium, tantalum, cobalt and iridium and wherein the predominant form of said titanium dioxide is anatase; and wherein the particles have a particle size distribution of up to 40%.

21. The method according to claim 20, wherein said particles are completely dispersed in said solvent.

22. The method according to claim 20, wherein said dispersion is applied by spin coating.

23. The method according to claim 20, further comprising the step of: d) allowing said solvent to evaporate.

24. The method according to claim 20, further comprising the step of: e) sintering said particles.

25. The method according to claim 20, wherein said dispersion of particles of metal oxide is provided by: b-i) performing controlled hydrolysis of $TiCl_4$ in water to obtain a colloid dispersion; and b-ii) performing dialysis of said colloidal dispersion.

26. The method according to claim 20, wherein the surface of the substrate comprises a native oxide.

27. The method according to claim 20, wherein the surface of the substrate body prior to step c) has been subjected to a roughening surface treatment, such as abrasive blasting and/or chemical etching.

28. The method according to claim 20, wherein said substrate body is turned.

29. The method according to claim 20, wherein the surface of said substrate body is polished.

30. The method according to claim 1, wherein said particles are packed together on the surface such that when said at least one layer results in a monolayer, the monolayer has an inherent porosity from at least 0.225*R with R being the average radius of the particles.

31. The method according to claim 1, wherein said particles are packed together on the surface such that when said at least one layer results in multilayers, the multilayers have an inherent porosity from at least 0.732*R with R being the average radius of the particles.

32. The method according to claim 20, wherein said particles are packed together on the surface such that when said at least one layer results in a monolayer, the monolayer has an inherent porosity from at least 0.225*R with R being the average radius of the particles.

33. The method according to claim 1, wherein said particles are packed together on the surface such that when said at least one layer results in multilayers, the multilayers have an inherent porosity from at least 0.732*R with R being the average radius of the particles.

* * * * *